(12) United States Patent
Fink et al.

(10) Patent No.: US 6,689,801 B2
(45) Date of Patent: Feb. 10, 2004

(54) CERTAIN HETEROARYL SUBSTITUTED THIOL INHIBITORS OF ENDOTHELIN-CONVERTING ENZYME

(75) Inventors: Cynthia A. Fink, Lebanon, NJ (US); Faribroz Firooznia, Eastchester, NY (US)

(73) Assignee: Novartis AG, Basel (CH)

( * ) Notice: Subject to any disclaimer, the term of this patent is extended or adjusted under 35 U.S.C. 154(b) by 42 days.

(21) Appl. No.: 10/171,321

(22) Filed: Jun. 13, 2002

(65) Prior Publication Data

US 2003/0018057 A1 Jan. 23, 2003

Related U.S. Application Data

(62) Division of application No. 09/690,061, filed on Oct. 16, 2000, now Pat. No. 6,426,354, which is a continuation of application No. PCT/EP99/02694, filed on Apr. 21, 1999.
(60) Provisional application No. 60/172,258, filed on Apr. 23, 1998.

(51) Int. Cl.[7] .......... A61K 31/44; A61K 38/00; C07D 333/10; C07D 213/00
(52) U.S. Cl. .......... 514/357; 514/183; 514/354; 514/19; 546/1; 546/279.7
(58) Field of Search .......... 514/357, 183, 514/354, 19; 546/1, 279.7

(56) References Cited

U.S. PATENT DOCUMENTS

| | | | |
|---|---|---|---|
| 5,432,186 A | 7/1995 | Fink | 514/357 |
| 5,506,244 A | 4/1996 | Fink | 514/354 |
| 5,508,266 A * | 4/1996 | Fink | 514/19 |
| 5,550,119 A | 8/1996 | De Lombaert et al. | 514/92 |
| 5,668,158 A | 9/1997 | Fink | 514/354 |
| 6,423,727 B1 | 7/2002 | De Lombaert et al. | 514/354 |
| 2002/0082218 A1 | 6/2002 | De Lombaert et al. | 514/354 |

FOREIGN PATENT DOCUMENTS

| | | |
|---|---|---|
| EP | 655 461 A | 5/1995 |
| WO | WO 95 12611 | 5/1995 |
| WO | WO 97/32849 | 9/1997 |
| WO | WO 97/32874 | 9/1997 |
| WO | WO 99/55723 | 11/1999 |
| WO | WO 99/55726 | 11/1999 |

OTHER PUBLICATIONS

Fink E.A., Journal of Medicinal Chemistry, vol. 39, No. 16, pp. 3158–3168 (1996).
Kukkola P.J. et al., Journal of Cardiovascular Pharmacology, vol. 26, No. Suppl. 03, pp. 565–568 (1995).
McKittrick et al., Bio–org. & Med.Chem., 6/14, pp. 1629–1634 (1996) Design & Syn . . . Endopeptidase 24.11.
Scheunemann et al., For. Rossendorf. Ber.FZR–200, pp. 18–20 (1997) also CAPLUS 1998:190635.
Bioorganic Med. Chem., vol. 6, (19), pp. 2317–2322 (1996).
Bioorganic Med. Chem., vol. 6, (14), pp. 1629–1634 (1996).
Derwent Abstract of WO 97/32874.
J.Med. Chem., vol. 38, pp. 5023–5038 (1995).
Tetrahedron Letters, vol. 38, pp. 7645–7648 (1997).
Deprez P. et al., Bioorganic & Medicinal Chemistry Letters, vol. 6, No. 19, pp. 2317–2322 (1996).
Balwierczak J.L. et al., Biochemical Pharmacology, vol. 49, No. 3, pp. 291–296 (1995).

\* cited by examiner

Primary Examiner—Mukund J. Shah
Assistant Examiner—Sudhaker B. Patel
(74) Attorney, Agent, or Firm—Norbert Gruenfeld

(57) ABSTRACT

Novel thiol derivatives of formula I

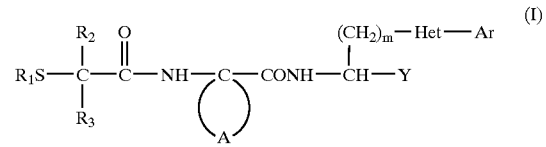

or of the formula Ia

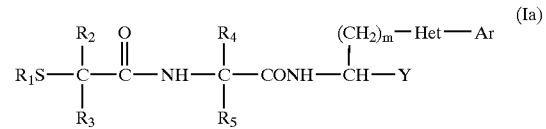

wherein the variables have the meanings as defined hereinbefore.

16 Claims, No Drawings

CERTAIN HETEROARYL SUBSTITUTED THIOL INHIBITORS OF ENDOTHELIN-CONVERTING ENZYME

This is a divisional of application Ser. No. 09/690,061 filed Oct. 16, 2000 now U.S. Pat. No. 6,426,354, which is a continuation of International Application No. PCT/EP 99/02694 filed Apr. 21, 1999 (designating the United States) which, in turn, claims the benefit of U.S. application Ser. No. 09/064,979 filed Apr. 23, 1998, which was converted to provisional application Ser. No. 60/172,258 filed on Apr. 23, 1998, now abandoned, said documents being incorporated herein by reference.

The present invention relates to the novel compounds described below which are useful as endothelin-converting enzyme (ECE) inhibitors in mammals.

The thiol derivatives described herein inhibit the formation of endothelin, reduce the plasma and tissue levels of endothelin and inhibit the biological effects of endothelin activity in mammals.

The compounds of the invention are thus useful for the treatment and/or prevention of endothelin dependent conditions and diseases, e.g. cardio- and cerebro-vascular disorders such as essential hypertension, vasoconstriction, congestive heart failure, pulmonary hypertension, cerebral ischemia (stroke), subarachnoid hemorrhage, traumatic brain injury, acute and chronic renal failure, atherosclerosis, cerebral vasospasm, vasoconstriction, arterial hypertrophy, restenosis, Raynaud's disease, myocardial infarction, obesity; also respiratory disorders such as bronchial asthma; gastrointestinal disorders such as inflammatory bowel disease, pancreatitis, emesis; also prostate hyperplasia, migraine, diabetes mellitus (diabetic nephropathy), preeclampsia, glaucoma and transplantation rejection, such as in aorta or solid organ transplantation; as well as erectile dysfunction.

The present invention is directed to the novel thiol derivatives of formula I

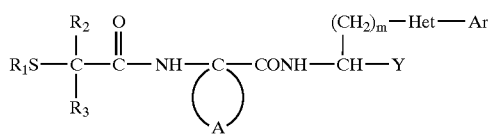

or of the formula Ia

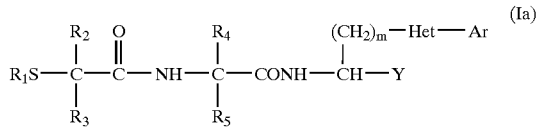

wherein

Het represents monocyclic heterocyclic aryl;

Ar represents carbocyclic or heterocyclic aryl;

$R_1$ represents hydrogen or acyl;

$R_2$ represents hydrogen, lower alkyl, carbocyclic or heterocyclic aryl, carbocyclic or heterocyclic aryl-lower alkyl, cycloalkyl, cycloalkyl-lower alkyl, biaryl, biaryl-lower alkyl, (hydroxy, lower alkoxy or acyloxy)-lower alkyl, or lower alkyl-(thio, sulfinyl or sulfonyl)-lower alkyl;

$R_3$ represents hydrogen or lower alkyl; or $R_2$ and $R_3$ together with the carbon atom to which they are attached represent cycloalkylidene or benzo-fused cycloalkylidene;

$R_4$ represents hydrogen, lower alkyl, substituted lower alkyl, aryl-lower alkyl or biaryl-lower alkyl;

$R_5$ represents lower alkyl, substituted lower alkyl, aryl-lower alkyl or biaryl-lower alkyl;

A together with the carbon atom to which it is attached forms a ring and represents 3 to 10 membered cycloalkylidene or 5 to 10 membered cycloalkenylidene radical which may be substituted by lower alkyl or aryl-lower alkyl or may be fused to a saturated or unsaturated carbocyclic 5-7-membered ring; or A together with the carbon to which it is attached represents 5 to 6 membered oxacycloalkylidene, thiacycloalkylidene or azacycloalkylidene optionally substituted by lower alkyl or aryl-lower alkyl; or A together with the carbon atom to which it is attached represents 2,2-norbonylidene;

m is zero or 1–3;

Y represents 5-tetrazolyl, carboxyl or carboxyl derivatized in form of a pharmaceutically acceptable ester;

disulfide derivatives derived from said compounds wherein $R_1$ is hydrogen; and pharmaceutically acceptable salts thereof; pharmaceutical compositions comprising said compounds; methods for preparation of said compounds; intermediates; and methods of treating disorders in mammals which are responsive to ECE inhibition by administration of said compounds to mammals in need of such treatment.

Pharmaceutically acceptable esters are preferably prodrug ester derivatives, such being convertible by solvolysis or under physiological conditions to the free carboxylic acids of formula I.

Encompassed by the instant invention are any prodrug derivatives of compounds of the invention having a free carboxyl, sulfhydryl or hydroxyl group, said prodrug derivatives being convertible by solvolysis or under physiological conditions to the free carboxyl, sulfhydryl and/or hydroxyl compounds. Prodrug derivatives are e.g. the esters of free carboxylic acids and S-acyl and O-acyl derivatives of thiols, or alcohols, wherein acyl has meaning as defined herein.

Pharmaceutically acceptable prodrug esters of carboxylic acids are preferably e.g. lower alkyl esters, cycloalkyl esters, lower alkenyl esters, aryl-lower alkyl esters, α-(lower alkanoyloxy)-lower alkyl esters such as the pivaloyloxymethyl ester, and α-(lower alkoxycarbonyl- or di-lower alkylamino carbonyl-)-lower alkyl esters.

Pharmaceutically acceptable salts are salts derived from pharmaceutically acceptable bases for any acidic compounds of the invention, e.g. those wherein Y represents carboxyl. Such are e.g. alkali metal salts (e.g. sodium, potassium salts), alkaline earth metal salts (e.g. magnesium, calcium salts), amine salts (e.g. tromethamine salts).

Compounds of the invention, depending on the nature of substituents, possess one or more asymmetric carbon atoms. The resulting diastereomers and optical antipodes are encompassed by the instant invention. Preferred is the configuration wherein the asymmetric carbon with the substituent Y has the S-configuration.

Preferred as endothelin converting enzyme inhibitors are the compounds with the S-configuration of formula II

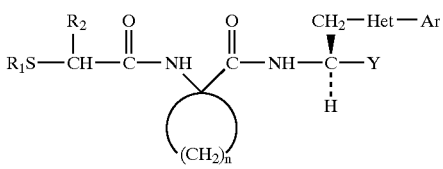

(II)

wherein Het represents monocyclic heterocyclic aryl; Ar represents monocyclic or bicyclic carbocyclic or heterocyclic aryl; $R_1$ represents hydrogen or carboxyl derived acyl; $R_2$ represents, lower alkyl, hydroxy-lower alkyl (lower alkylthio- or lower alkoxy-)lower alkyl, carbocyclic or heterocyclic aryl, carbocyclic or heterocyclic aryl-lower alkyl, cycloalkyl, cycloalkyl-lower alkyl, or biaryl-lower alkyl; Y represents 5-tetrazolyl, carboxyl or carboxyl derivatized in form of a pharmaceutically acceptable ester; n represents 2–6, preferably 2, 4 or 5; disulfide derivatives derived from said compounds wherein $R_1$ is hydrogen; and pharmaceutically acceptable salts thereof.

Further preferred are said compounds of formula II wherein Het is thienyl, furanyl, oxazolyl, pyridyl, thiazolyl or oxadiazolyl, each optionally substituted by lower alkyl; Ar is monocyclic carbocyclic aryl or monocyclic heterocyclic aryl; $R_1$ represents hydrogen, aryl-lower alkanoyl, lower alkanoyl, lower alkoxy-lower alkanoyl, or heterocyclic or carbocyclic aroyl; $R_2$ represents $C_2$–$C_4$ alkyl interrupted by S or O, $C_2$–$C_5$-alkyl or cyclohexylmethyl; Y represents 5-tetrazolyl, carboxyl, lower alkoxycarbonyl, carbocyclic or heterocyclic aryl-lower alkoxycarbonyl, α-(lower alkanoyloxy-, lower alkoxycarbonyl- or di-lower alkylaminocarbonyl-)lower alkoxycarbonyl; n is 2, 4 or 5; and pharmaceutically acceptable salts thereof.

Particularly preferred as endothelin converting enzyme inhibitors are said compounds with the S-configuration of formula III

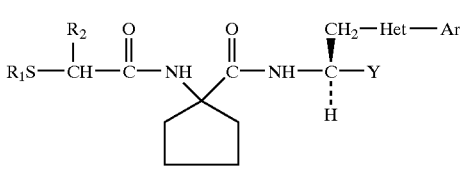

(III)

and of formula IIIa

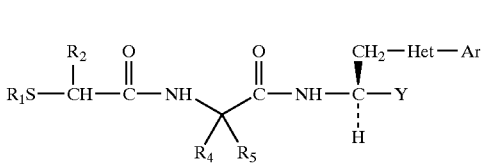

(IIIa)

wherein Het represents pyridyl, pyrimidinyl, thienyl, furanyl, oxazolyl, isoxazolyl, oxadiazolyl or thiazolyl, each optionally substituted by lower alkyl;

Ar represents monocyclic carbocyclic aryl or monocyclic heterocyclic aryl;

$R_1$ represents hydrogen, lower alkanoyl, methoxy-lower alkanoyl, benzoyl or pyridylcarbonyl;

$R_2$ represents $C_2$–$C_5$-alkyl, cyclohexylmethyl or $C_2$–$C_4$-alkyl interrupted by O or S;

$R_4$ and $R_5$ represent lower alkyl or lower alkyl substituted by lower alkoxycarbonyl, lower alkanoyloxy, lower alkanoylthio, lower alkoxy, lower alkylthio, hydroxy, di-lower alkylamino, lower alkanoylamino, morpholino, piperidino, pyrrolidino or 1-lower alkylpiperazino;

Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; and pharmaceutically acceptable salts thereof.

A further embodiment of the invention relates to the compounds with the S-configuration of formula IIIb

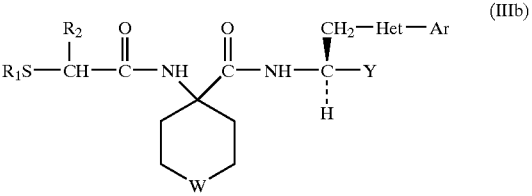

(IIIb)

wherein Het represents pyridyl, pyrimidinyl, thienyl, furanyl, oxazolyl, isoxazolyl, oxadiazolyl or thiazolyl, each optionally substituted by lower alkyl;

Ar represents monocyclic carbocyclic aryl or monocyclic heterocyclic aryl;

W represents $CH_2$, O, S or $NR_6$ in which $R_6$ is hydrogen, acyl, lower alkyl or aryl-lower alkyl;

$R_1$ represents hydrogen, lower alkanoyl, methoxy-lower alkanoyl, benzoyl or pyridylcarbonyl;

$R_2$ represents $C_2$–$C_5$-alkyl, cyclohexylmethyl or $C_2$–$C_4$-alkyl interrupted by O or S;

Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; and pharmaceutically acceptable salts thereof.

Further preferred are said compounds of formula I, Ia, II, III, IIIa or IIIb wherein Het represents 3-pyridyl, 2-, 4- or 5-pyrimidinyl, 2- or 3-thienyl, 2- or 3-furanyl, 4- or 5-oxazolyl, 3-, 4- or 5-isoxazolyl or 4- or 5- thiazolyl, each optionally substituted by lower alkyl; Ar represents monocyclic carbocyclic or heterocyclic aryl; $R_1$ represents hydrogen or lower alkanoyl; $R_2$ represents $C_3$–$C_5$-alkyl; Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; and pharmaceutically acceptable salts thereof.

A particular preferred embodiment alternatively relates to the compounds of formula III or IIIa wherein Het represents pyridyl, thienyl, oxazolyl, oxadiazolyl or thiazolyl each optionally substituted by lower alkyl; Ar represents phenyl or phenyl substituted by one or more substituents selected from the group consisting of halogen, lower alkoxy, nitro, amino and lower alkanoyl-amino; $R_1$ represents hydrogen or lower alkanoyl; $R_2$ represents lower alkyl or lower alkyl substituted by lower alkylthio, phenyl, phenyl substituted by hydroxy, or cyclohexyl; $R_4$ is hydrogen or lower alkyl; $R_5$ is lower alkyl, phenyl-lower alkyl or pyridyl-lower alkyl in which the pyridyl moiety is substituted by halogen or thienyl; and Y represents carboxyl or lower alkoxycarbonyl; or a pharmaceutically acceptable salt thereof.

A particular preferred embodiment relates to the compounds of formula II, III, IIIa and IIIb wherein Het represents 3-pyridyl; Ar represents monocyclic carbocyclic or monocyclic heterocyclic aryl; $R_1$ represents hydrogen; $R_2$ represents $C_3$–$C_5$-alkyl, cyclohexylmethyl or $C_2$–$C_4$-alkyl interrupted by O or S; $R_4$ and $R_5$ represent lower alkyl (for compound of formula IIIa); Y represents carboxyl; ester and/or S-acyl prodrug derivatives thereof; and pharmaceutically acceptable salts thereof.

Particularly preferred are said compounds wherein Het represents 3-pyridyl; Ar represents phenyl or phenyl substituted by halogen, lower alkyl, lower alkoxy, nitro, amino or acylamino; or Ar represents 2- or 3-furanyl, 2- or 3-thienyl, 2- 4- or 5-thiazolyl, 3-pyridyl, 2- 4- or 5-oxazolyl, or 5-pyrimidinyl; $R_1$ represents hydrogen or lower alkanoyl; $R_2$ represents $C_3$–$C_5$-alkyl, cyclohexylmethyl, or $C_2$–$C_4$-alkyl interrupted by O or S; $R_4$ and $R_5$ (for compound of formula IIIa) represent $C_1$–$C_4$- straight chain alkyl; Y is 5-tetrazolyl, carboxyl or lower alkoxycarbonyl; and pharmaceutically acceptable salts thereof.

Further preferred are the compounds of formula

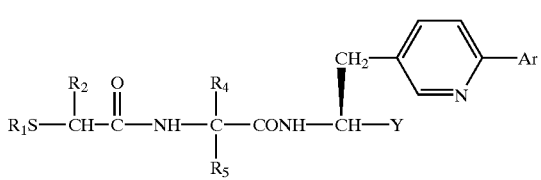

(IIIc)

and of the formula

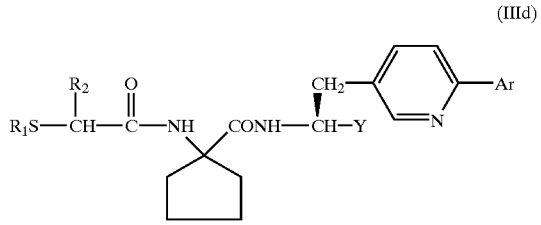

(IIId)

wherein
Ar represents monocyclic carbocyclic aryl, 2- or 3-thienyl, 3-pyridyl, 5-pyrimidinyl, 2-thiazolyl, 2-oxazolyl, 3-isoxazolyl, 2- or 3- furanyl, each optionally substituted by lower alkyl;
$R_1$ represents hydrogen or lower alkanoyl;
$R_2$ represents $C_3$–$C_5$-alkyl, cyclohexylmethyl or $C_2$–$C_4$-alkyl interrupted by O or S;
Y represents carboxyl or lower alkoxycarbonyl;
$R_4$ and $R_5$ represent lower alkyl (for compounds of formula IIIc);
and pharmaceutically acceptable salts thereof.

Particularly preferred are said compounds of formula IIIc and IIId wherein Y represents carboxyl or lower alkoxycarbonyl; $R_1$ represents hydrogen or lower alkanoyl; $R_2$ represents n-propyl, isopropyl, n-butyl or isobutyl; $R_4$ and $R_5$ (for compounds of formula IIIc) are identical and represent methyl or ethyl; and Ar represents phenyl or phenyl substituted by halo, lower alkyl, lower alkoxy, nitro, amino, or acylamino; or Ar represents 2- or 3-thienyl, 3-pyridyl, 5-pyrimidinyl, 2- or 3-furanyl or 2-thiazolyl; and pharmaceutically acceptable salts thereof.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, nitro, trifluoromethyl, amino, acylamino e.g. lower alkanoylamino, lower alkyl-(thio, sulfinyl or sulfonyl), lower alkoxycarbonyl, mono- or di-lower alkylcarbamoyl, or mono- or di-lower alkylamino.

Bicyclic carbocyclic aryl represents 1- or 2-naphthyl or 1- or 2-naphthyl preferably substitued by lower alkyl, lower alkoxy or halogen.

Monocyclic heterocyclic aryl represents preferably optionally substituted thiazolyl, thienyl, furanyl, pyridyl, pyrimidinyl, oxazolyl, isoxazolyl, pyrrolyl, imidazolyl or oxadiazolyl.

Monocyclic heterocyclic aryl for the groups Het and/or Ar in the above formulae is preferably optionally substituted pyridyl (e.g. 3- or 4-pyridyl), thienyl (e.g. 2- or 3-thienyl), oxazolyl (e.g. 2- 4- or 5-oxazolyl), thiazolyl (e.g. 2-, 4- or 5-thiazolyl), oxadiazolyl (e.g. 3-[1,2,4] oxadiazolyl), furanyl (e.g. 2- or 3-furanyl), isoxazolyl (e.g. 4-isoxazolyl) or pyrimidinyl (e.g. 5-pyrimidinyl).

The combined groups Ar-Het in the above formulae represent for example optionally substituted 5-Ar-(2- or 3-thienyl), 5-Ar-(2- or 3-furanyl), 2-Ar-(4- or 5- oxazolyl), 2-Ar-(4-5-thiazolyl), 5-Ar-(3-[1,2,4]oxadiazolyl) or 6-Ar-3-pyridyl in which Ar is carbocyclic or heterocyclic aryl as defined herein.

Illustrative of the invention, Ar-Het combined represents for example 5-phenyl-2-thienyl, 4-phenyl-2-thienyl, 4-methyl-2-phenyl-5-oxazolyl, 2-(3-chloro-4-fluorophenyl)-5-thiazolyl, 5-(3,5-dimethyl-4-isoxazolyl)-3-[1,2,4]oxadiazolyl, 6-(3-thienyl)-3-pyridinyl, 6-(3-pyridinl)-3-pyridinyl, 6-(-thienyl)-3-pyridinyl, 6-(3-furanyl)-3-pyridinyl, 6-(3-nitrophenyl)-3-pyridinyl, 6-(3-acetylaminophenyl)-3-pyridinyl, 6-(3-aminophenyl)-3-pyridinyl, 6-(2-furanyl)-3-pyridinyl, 6-(2-thiazolyl)-3-pyridinyl, 6-(2-methoxyphenyl)-3-pyridinyl, 6-phenyl-3-pyridinyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl or hydroxy-lower alkyl.

Optionally substituted thiazolyl represents e.g. 4-thiazolyl, or 4-thiazolyl substituted by lower alkyl.

Optionally substituted pyrimidinyl represents 2-, 4- or 5-pyridridinyl or 2-, 4- or 5-pyrimidinyl preferably substituted by lower alkyl.

Optionally substituted oxazolyl represents 2-, 4- or 5-oxazolyl or 2-, 4- or 5-oxazolyl preferably substituted by lower alkyl.

Optionally substituted isoxazolyl represents 3-, 4- or 5-isoxazolyl or 3-, 4- or 5-isoxazolyl preferably substituted by lower alkyl.

Optionally substituted pyrrolyl represents 1-, 2- or 3-pyrrolyl or 1-, 2- or 3- pyrrolyl preferably substituted by lower alkyl.

Optionally substituted imidazolyl represents 1-, 2- or 4-imidazolyl or 1-, 2- or 4-imidazolyl preferably substituted by lower alkyl.

Optionally substituted oxadiazolyl represents 3- or 5- [1, 2, 4] oxadiazolyl preferably substituted by lower alkyl.

Bicyclic heterocyclic aryl represents preferably benzothiophenyl, benzofuranyl, indolyl or benzothiazolyl optionally substituted by hydroxy, lower alkyl, lower alkoxy or halogen, advantageously 3-indolyl, 2-benzothiazolyl, 2-benzofuranyl or 3-benzo[b]thiophenyl.

Aryl in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up to and including 4 and advantageously one or two carbon atoms. Such may be straight chain or branched.

A lower alkyl group preferably contains 1–4 carbon atoms and represents for example ethyl, propyl, butyl or advantageously methyl.

Substituted lower alkyl for example represents lower alkyl substituted by lower alkoxycarbonyl, lower alkanoyloxy, lower alkanoylthio, lower alkoxy, or by lower alkylthio; also lower alkyl substituted by e.g. hydroxy, di-lower alkylamino, lower alkanoylamino, morpholino, piperidino, pyrrolidino or 1-lower alkylpiperazino.

A lower alkoxy group preferably contains 1–4 carbon atoms and represents for example methoxy, propoxy, isopropoxy or advantageously ethoxy.

Cycloalkyl represents a saturated cyclic hydrocarbon radical which preferably contains 5 to 7 ring carbons, preferably cyclopentyl or cyclohexyl.

The term cycloalkyl(lower) alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Cycloalkylidene is 3 to 10 membered, preferably 3, 5 or 6-membered, and represents a cycloalkane linking group e.g. cyclopropylidene, cyclopentylidene, cyclohexylidene, cycloheptylidene or cyclooctylidene, in which the two attached groups are attached to the same carbon of the cycloalkane ring.

Cycloalkenylidene is 5 to 10 membered, prefereably 5 or 6-membered, and represents a cycloalkene linking group in which the two attached groups are attached to the same carbon atom of the cycloalkene ring.

Cycloalkylidene fused to a saturated carbocyclic ring represents e.g. perhydronaphthylidene.

Cycloalkylidene fused to an unsaturated carbocyclic ring represents e.g. 1,1- or 2,2-tetralinylidene or 1,1- or 2,2-indanylidene.

5 or 6 Membered oxacycloalkylidene represents preferably a tetrahydrofuran or tetrahydropyran linking group, e.g. tetrahydrofuranylidene or tetrahydropyranylidene, in which the two attached groups are attached to the same carbon atom of the respective rings, e.g. at the 3 or 4 position thereof.

5 or 6 Membered thiacycloalkylidene represents preferably a tetrahydrothiophene or tetrahydrothiopyran linking group in which the two attached groups are attached to the same carbon atom of the respective rings, e.g. at the 3 or 4 position thereof.

5 or 6 Membered azacyloalkylidene represents preferably a pyrrolidine or piperidine linking groups in which the two attached groups are attached to the same carbon atom of the respective rings, e.g. at the 3 or 4 position thereof, and the nitrogen may be substituted by lower alkyl, e.g. methyl, or by aryl-lower alkyl, e.g. benzyl.

Halogen (halo) preferably represents fluoro or chloro, but may also be bromo or iodo.

Acyl is derived from a carboxylic acid and represents preferably optionally substituted lower alkanoyl, cycloalkylcarbonyl, carbocyclic aryl-lower alkanoyl, aroyl, lower alkoxycarbonyl or aryl-lower alkoxycarbonyl, advantageously optionally substituted lower alkanoyl or aroyl.

Lower alkanoyl is preferably acetyl, propionyl, butanoyl, pentanoyl, or pivaloyl.

Optionally substituted lower alkanoyl for example represents lower alkanoyl or lower alkanoyl substituted by lower alkoxycarbonyl, lower alkanoyloxy, lower alkanoylthio, lower alkoxy, or by lower alkylthio; also lower alkanoyl substituted by e.g. hydroxy, di-lower alkylamino, lower alkanoylamino, morpholino, piperidino, pyrrolidino or 1-lower alkylpiperazino.

Aroyl is carbocyclic or heterocyclic aroyl, preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Azacycloalkyl represents preferably piperidyl, advantageously 3-piperidyl optionally substituted on nitrogen by lower alkyl or acyl.

Acyloxy is preferably optionally substituted lower alkanoyloxy, lower alkoxycarbonyloxy, monocyclic carbocyclic aroyloxy or monocyclic heterocyclic aroyloxy; also carbocyclic or heterocyclic aryl-lower alkanoyloxy.

Optionally substituted lower alkanoyloxy is preferably lower alkanoyloxy, such as acetyloxy, substituted by any group indicated above under optionally substituted alkanoyl.

Aryl-lower alkoxycarbonyl is preferably monocyclic carbocyclic-lower alkoxycarbonyl, advantageously benzyloxycarbonyl.

Biaryl represents for example 4-biphenylyl.

Biaryl-lower alkyl is preferably 4-biphenylyl-lower alkyl, advantageously 4-biphenylyl-methyl.

The novel compounds of the invention are pharmacologically potent endothelin converting enzyme inhibitors which inhibit the formation of endothelin in mammals. They thus inhibit the biological effects of endothelin in mammals.

The compounds of the invention are thus particularly useful in mammals for the treatment of e.g. hypertension and heart failure, cerebrovascular disorders, e.g. cerebral vasospasm and stroke, acute or chronic renal failure, erectile dysfunction, pulmonary disorders e.g. bronchial asthma, and complications associated with organ transplantation.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-5}$ molar and $10^{-9}$ molar concentrations. The dosage in vivo may range depending on the route of administration, between about 0.1 and 50 mg/kg, advantageously between about 1.0 and 25 mg/kg.

The in vitro inhibition of endothelin-converting enzyme can be determined as follows:

The test compound is dissolved in dimethyl sulfoxide or 0.25 M sodium bicarbonate solution, and the solution is diluted with a pH 7.4 buffer to the desired concentration.

Endothelin converting enzyme (ECE) is partially purified from porcine primary aortic endothelial cells by DE52 anion exchange column chromatography and its activity is quantified by radioimmunoassay as described in Anal. Biochem. 212, 434–436 (1993). Alternatively, the native enzyme can be substituted by a recombinant form of ECE, as described, for example in Cell 78, 473–485 (1994). Human ECE-1 has been described by several groups (Schmidt, M. et al. FEBS Letters, 1994, 356, 238–243; Kaw, S.; Emoto, N.; Jeng, A.; Yanagisawa, M. 4th Int. Conf. on Endothelin; April 23–25, London (UK), 1995; C6; Valdenaire, O. et al. J. Biol. Chem. 1995, 270, 29794–29798; Shimada, K. et al. Biochem. Biophys. Res. Commun., 1995, 207, 807–812). The ECE inhibiton can be determined as described in Biochem. Mol. Biol. Int. 31, (5), 861–867 (1993), by radioimmunoassay to measure ET-1 formed from big ET-1.

Alternatively, recombinant human ECE-1 (rhECE-1) can be used, as follows:

Chinese hamster ovary cells expressing recombinant human endothelin converting enzyme-1 (rhECE-1; Kaw, S.; Emoto, N.; Jeng, A.; Yanagisawa, M. 4th Int. Conf. on Endothelin; April 23–25, London (UK), 1995; C6) are cultured in DMEM/F12 medium containing 10% fetal bovine serum and 1× antibiotic-antimycotic. Cells are harvested by scraping, pelleted by centrifugation, and homogenized at 4° C. in a buffer containing 5 mM $MgCl_2$., 1 $\mu$M pepstatin A, 100 $\mu$M leupeptin, 1 mM PMSF, and 20 mM Tris, pH 7.0, with a ratio of 2 mL of buffer/mL of cells. The cell debris is removed by brief centrifugation, and the supernatant is centrifuged again at 100,000×g for 30 minutes. The resulting pellet is resuspended in a buffer containing 200 mM NaCl and 50 mM Tes, pH 7.0, at a protein concentration about 15 mg/mL and stored in aliquots at −80° C.

To assess the effect of an inhibitor on ECE-1 activity, 10 $\mu$g of protein is pre-incubated with the compound at a desired concentration for 20 min at room temperature in 50 mM TES, pH 7.0, and 0.005% Triton X-100 in a volume of 10 $\mu$L. Human big ET-1 (5 $\mu$L) is then added to a final concentration of 0.2 $\mu$M, and the reaciton mixture is further incubated for 2 h at 37° C. The reaction is stopped by adding 500 $\mu$L of radioimmunoassay (RIA) buffer containing 0.1% Triton X-100, 0.2% bovine serum albumin, and 0.02% $NaN_3$ in phosphate-buffered saline.

Diluted samples (200 $\mu$L) obtained from the above enzyme assay are incubated at 4° C. overnight with 25 $\mu$L each of [$^{125}$I]ET-1 (10,000 cpm/tube) and 1:20,000-fold diluted rabbit antibodies that recognize specifically the carboxyl terminal tryptophan of ET-1. Goat anti-rabbit antibodies coupled to magnetic beads (70 $\mu$g) are then added to each tube, and the reaction mixture is further incubated for 30 min at room temperature. The beads are pelleted using a magnetic rack. The supernatant is decanted, and the radioactivity in the pellet is counted in a gamma counter. Total and nonspecific binding are measured in the absence of nonradioactive ET-1 and anti-ET antibodies, respectively. Under these conditions, ET-1 and big ET-1 displace [$^{125}$I]ET-1 binding to the antibodies with $IC_{50}$ values of 21±2 and 260,000±66,000 fmol (mean±SEM, n=3–5), respectively.

In order to determine the $IC_{50}$ value of an inhibitor, a concentration-response curve of each inhibitor is determined. An IBM-compatible version of ALLFIT program is used to fit data to a one-site model.

In vitro testing is most appropriate for the compounds wherein Y is 5-tetrazolyl or carboxyl.

Illustrative of the invention, the compound of Example 2(s) demonstrates an $IC_{50}$ of about 4 nM in the in vitro assay for rh-ECE-1 inhibition.

Endothelin converting enzyme inhibition can also be determined in vivo by measuring the inhibition of big ET-1-induced pressor response in the anesthesized or conscious rat, as described below. The effect of the inhibitors on the pressor response resulting from big ET-1 challenge is measured in Sprague-Dawley rats as described in Biochem. Mol. Biol. Int. 31, (5), 861–867 (1993). Results are expressed as percent inhibition of the big ET-1-induced pressor response as compared to vehicle.

Male Sprague-Dawley rats are anesthetized with Inactin (100 mg/kg i.p.) and instrumented with catheters in the femoral artery and vein to record mean arterial pressure (MAP) and administer compounds, respectively. A tracheostomy is performed and a cannula inserted into the trachea to ensure airway patency. The body temperature of the animals is maintained at 37±1° C. by means of a heating blanket. Following surgery, MAP is allowed to stabilize before interrupting autonomic neurotransmission with chlorisondamine (3 mg/kg i.v.). Rats are then treated with the test compound at 10 mg/kg i.v. or vehicle and challenged with big ET-1 (1 nmol/kg i.v.) 15 min and 90 min later. Generally, the data are reported as the maximum increase in MAP produced by big ET-1 in animals treated with the test compound or vehicle.

Male Sprague-Dawley rats are anesthetized with methohexital sodium (75 mg/kg i.p.) and instrumented with catheters in the femoral artery and vein to measure mean arterial pressure (MAP) and administer drugs, respectively. The catheters are threaded through a swivel system that enables the rats to move freely after regaining consciousness. The rats are allowed to recover from this procedure for 24 h before initiating the study. On the following day, MAP is recorded via the femoral artery catheter and a test compound or vehicle is administered via the femoral vein. Animals are challenged with big ET-1 at 1 nmol/kg i.v. at various times after dosing. After an adequate washout period, depending upon the dose and regimen, animals can be re-tested at another dose of test compound or vehicle. Generally, the data are reported as the change in MAP produced by big ET-1 at 2-minute intervals in animals treated with the test compound as compared to vehicle.

ECE inhibition can also be determined in vivo by measuring the inhibition of the big ET-1 induced pressor response in conscious spontaneously hypertensive rats (SHR), e.g. as described in Biochem. Biophys. Res. Commun. 204, 407–412 (1994).

Male SHR (16–18 weeks of age) are administered either test compound or vehicle (1 M $NaHCO_3$) via an osmotic minipump implanted subcutaneously. On day 5 femoral arterial and venous catheters are placed in anesthetized rats for the measurement of MAP and for test compound administration, respectively. After a 48 hour recovery period, MAP is recorded (day 7) through the arterial catheter connected to a pressure transducer. Blood pressure and heart rate are allowed to stabilize for 30 min before ganglion blockade is performed using chlorisondamine (10 mg/kg i.v.). Approximately 15 min later, a bolus dose of big ET-1 (0.25 nmol/kg i.v.) is administered to both vehicle- and test compound treated rats. The change in blood pressure in response to big ET-1 is then compared between the two groups of rats at 1, 5, 10, 15, 30 and 60 min after dosing using a two-way ANOVA.

The compounds of the invention inhibit cerebrovascular constriction and are useful for the treatment and alleviation of cerebral spasm. They are thus in turn useful for the treatment and alleviation of conditions in which cerebral vasospasm occurs. Such conditions include stroke, cerebral ischemia, acute and traumatic brain injury, brain hemorrhage, in particular aneurysmal subarachnoid hemorrhage, as well as migraine.

The inhibition of cerbral vasospasm is demonstrated by measuring the inhibition of experimentally induced constriction of basilar cerebral arteries in the rabbit (Caner et al., J. Neurosurg., 1996, 85, 917–922).

Bronchial effects can be determined by measuring the effect in a model of ET-1 induced bronchoconstriction.

Compounds of the invention also possess angiotensin converting enzyme (ACE) and neutral endopeptidase (NEP) inhibitory activity. Tests for determination thereof are described e.g. in U.S. Pat. No. 5,506,244 which is incorporated herein by reference.

The combined effect is beneficial for e.g. the treatment of cardiovascular disorders in mammals such as hypertension, congestive heart failure and renal failure.

The compounds of the invention can generally be prepared according to methodology described in U.S. Pat. No. 5,506,244, in particular using the processes described and illustrated below for the compounds of formula I, e.g.

(a) by condensing a compound of formula IV

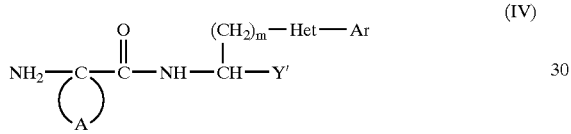

wherein the symbols Het, Ar, m and A have the meaning as defined above and Y' represents N-protected 5-tetrazolyl or esterified carboxyl, with a carboxylic acid of the formula V

or a reactive functional derivative thereof, wherein $R_2$ and $R_3$ have meaning as defined above, $R_1'$ represents a labile S-protecting group, e.g. acyl, t-butyl or optionally substituted benzyl; or (b) by condensing a compound of the formula VI

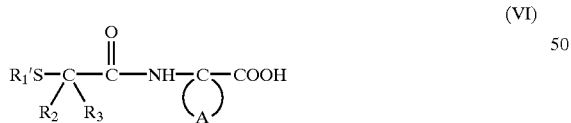

or a reactive functional derivative thereof wherein the symbols A, $R_1'$, $R_2$ and $R_3$ have meaning as defined above, with a compound of the formula VII

wherein Het, Ar, m and Y' have meaning as defined above; or (c) by condensing under basic conditions a compound of the formula

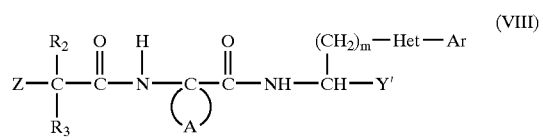

wherein the symbols Het, Ar, A, $R_2$, $R_3$, and Y' have meaning as defined above and Z represents a reactive esterified hydroxyl group (e.g. chloro or bromo) as a leaving group, with a compound of the formula

wherein $R_1'$ represents a labile S-protecting group, e.g. acyl, t-butyl or optionally substituted benzyl;

and converting a resulting product wherein $R_1'$ is optionally substituted benzyl to a compound of formula I wherein $R_1$ is hydrogen; and in above said process, if temporarily protecting any interfering reactive group (s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are converted to the compounds of the invention in manner described herein, functional groups present, such as thiol, carboxyl, amino and hydroxyl groups, are optionally protected by conventional protecting groups that are common in preparative organic chemistry. Protected thiol, carboxyl, amino and hydroxyl groups are those that can be converted under mild conditions into free thiol, carboxyl, amino and hydroxyl groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P. G. M. Woots, "Protective Groups in Organic Synthesis", Wiley, N.Y. 1991, "The Peptides", Vol. I, Schroeder and Luebke, Academic Press, London, N.Y., 1965, and also in P. J. Kocienski, "Protecting Groups", Thieme, N.Y. 1994.

Suitable protecting groups for the preparation of the 5-tetrazolyl compounds are the protecting groups customarily used in tetrazole chemistry, especially triphenylmethyl, unsubstituted or substituted, (for example nitro-substituted), benzyl such as 4-nitrobenzyl, lower alkoxymethyl such as methoxy- and ethoxymethyl, also 1-ethoxyethyl, lower alkylthiomethyl such as methylthiomethyl, silyl such as tri-lower alkylsilyl, for example dimethyl-tert-butyl- and triisopropylsilyl, and also 2-cyanoethyl, also lower alkoxy-lower alkoxy-methyl, such as 2-methoxyethoxymethyl, benzyloxymethyl and phenacyl.

The removal of the protecting groups is carried out in accordance with known methods. For example, the triphenylmethyl group is customarily removed by hydrolysis, especially in the presence of an acid, or by hydrogenolysis in the presence of a hydrogenation catalyst; 4-nitrobenzyl is removed, for example, by hydrogenolysis in the presence of a hydrogenation catalyst; methoxy- or ethoxy-methyl is removed, for example, by treatment with a tri-lower alkyl-, such as triethyl- or tributyl-tin bromide; methylthiomethyl is removed, for example, by treatment with trifluoroacetic acid; silyl radicals are removed, for example, by treatment with fluorides, such as tetra-lower alkyl-ammonium fluorides, for example tetrabutylammonium fluoride, or alkali metal fluorides, for example sodium fluoride; 2-cyanoethyl is removed, for example, by hydrolysis, for example with sodium hydroxide solution; 2-methoxyethoxymethyl is removed, for example, by hydrolysis, for example with hydrochloric acid; and benzyloxymethyl and phenacyl are removed, for example, by hydrogenolysis in the presence of a hydrogenation catalyst.

A tetrazole protecting group, which is preferably introduced by conversion of a similarly protected amide to the corresponding N-substituted tetrazole, is e.g. cyanoethyl, p-nitrophenylethyl, lower alkoxycarbonylethyl, phenylsulfonylethyl and the like. Such tetrazole protecting groups can be removed by a retro-Michael deblocking reaction with a base such as DBN (1,5-diazabicyclo[4.3.0]non-5-ene), an amidine, an alkali metal carbonate or alkoxide, e.g. potassium carbonate, potassium t-butoxide, sodium methoxide in an inert solvent.

An amino protecting group is preferably t-butoxycarbonyl or benzyloxycarbonyl.

A sulfhydryl protecting group is preferably lower alkanoyl, e.g. acetyl.

The preparation of compounds of the invention according to process (a) involving the condensation of an amine of formula IV with the acid of formula V or a functional reactive derivative thereof, is carried out by methodology well-known for peptide synthesis.

The condensation according to process (a) of a compound of formula IV with a free carboxylic acid of formula V is carried out advantageously in the presence of a condensing agent such as dicyclohexylcarbodiimide or N-(3-dimethylaminopropyl)-N'-ethylcarbodiimide, and hydroxybenzotriazole, 1-hydroxy-7-azabenzotriazole, chlorodimethoxytriazine or benzotriazol-1-yloxy-tris-(dimethylamino)-phosphonium hexafluorophosphate (BOP Reagent), and triethylamine or N-methylmorpholine, in an inert polar solvent such as dimethylformamide or methylene chloride, preferably at room temperature.

The condensation of a compound of formula IV with a reactive functional derivative of an acid of formula V in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine, N-methylmorpholine or pyridine, preferably at room temperature.

Reactive functional derivatives of carboxylic acids of formula V are preferably acid halides (e.g. the acid chloride) and mixed anhydrides, such as the pivaloyl or isobutyloxycarbonyl anhydride, or activated esters such as benzotriazole, 7-azabenzotriazole or hexafluorophenyl ester.

The starting materials of formula IV can be prepared according to methods described herein and illustrated in the examples.

The preparation of a starting material of formula IV involves the acylation of an ester of the amino acid of formula X

(X)

wherein Het, Ar, m and Y' have meaning as defined hereinabove with an appropriately N-protected cyclic amino acid (or a reactive functional derivative) of formula XI

(XI)

wherein A has meaning as defined hereinabove and $R_7$ is a labile amino protecting group, e.g. t-butoxycarbonyl, to obtain the corresponding N-protected compound of formula IV.

The condensation of a compound of formula X with a compound of formula XI is carried out by methodology well known in peptide synthesis, e.g. as described above for the condensation of a compound of formula IV with a compound of formula V. The N-protecting group is removed according to methods well-known in the art, e.g. the t-butoxycarbonyl is removed with anhydrous acid such as trifluoroacetic acid.

The starting amino acids and esters of compounds of formula X and XI are either known in the art or if new can be prepared according to methods well-known in the art. The α-amino acids of formula X are preferably obtained as the —S— enantiomers. Resolution of N-acyl amino acid esters can be performed by hydrolysis with an esterase, e.g. alcalase, to give the S-amino acid.

The biaryl aminoacids of formula X (or subsequent intermediates) can be prepared e.g. from the corresponding protected halo-substituted heteroaryl aminoacids under the conditions of a palladium-catalyzed Suzuki coupling reaction using the appropriate arylboronate or under the conditions of a palladium-catalyzed Stille coupling reaction using the appropriate arylstannane.

The starting materials of formula V are known or if new may be prepared according to conventional methods. The starting materials are prepared e.g. from the corresponding racemic or optically active α-amino acids, by conversion thereof to the α-bromo derivative followed by displacement thereof with the appropriate thio acids or optionally substituted benzylthiol, under basic conditions, for example as illustrated in European Patent application No. 524,553 published Jan. 27, 1993. S-Debenzylation of the resulting final products is carried out by reductive cleavage, e.g. with sodium in ammonia. S-Deacylation is carried out by e.g. base catalyzed hydrolysis with dilute aqueous sodium hydroxide or lithium hydroxide.

The preparation of the compounds of the invention according to process (b) involving the condensation of an acid of formula VI with a compound of formula VII is carried out in a similar fashion to process (a). Similarly the starting materials of formula VI are prepared by condensation of an acid of formula V with an ester corresponding to cyclic amino acids of formula XI ($R_7$ being hydrogen) under conditions similar to those described above, followed by removal of the carboxyl or tetrazolyl protecting group.

The preparation of the compounds of the invention according to process (c) involving the displacement of a leaving group Z in a compound of formula VII with a sulfhydryl derivative $R_1'$—SH is carried out according to methods well-known in the art.

A reactive esterified hydroxyl group, represented by Z, is a hydroxyl group esterified by a strong inorganic or organic acid. Corresponding Z groups are in particular halo, for example chloro, bromo or iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The displacement is carried out in an inert solvent, such as dimethylformamide, methylene chloride or THF in the presence of a base such as potassium carbonate, triethylamine, diisopropylethylamine, N-methylmorpholine, and the like at room or elevated temperatures.

Similarly, the starting materials of formula VIII can be prepared by reacting the amide derivative of formula IV with an acid of the formula

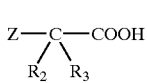

(XII)

wherein $R_2$ and $R_3$ and Z have meaning as defined above, under conditions described for process (a).

Acids of formula XII e.g. wherein Z is bromo, can be prepared from the corresponding α-aminoacids according to methods well known in the art. Optically active acids of formula XII can be obtained from optically active α-aminoacids as illustrated herein.

The following sequences of reactions are illustrative of process (c).

A:

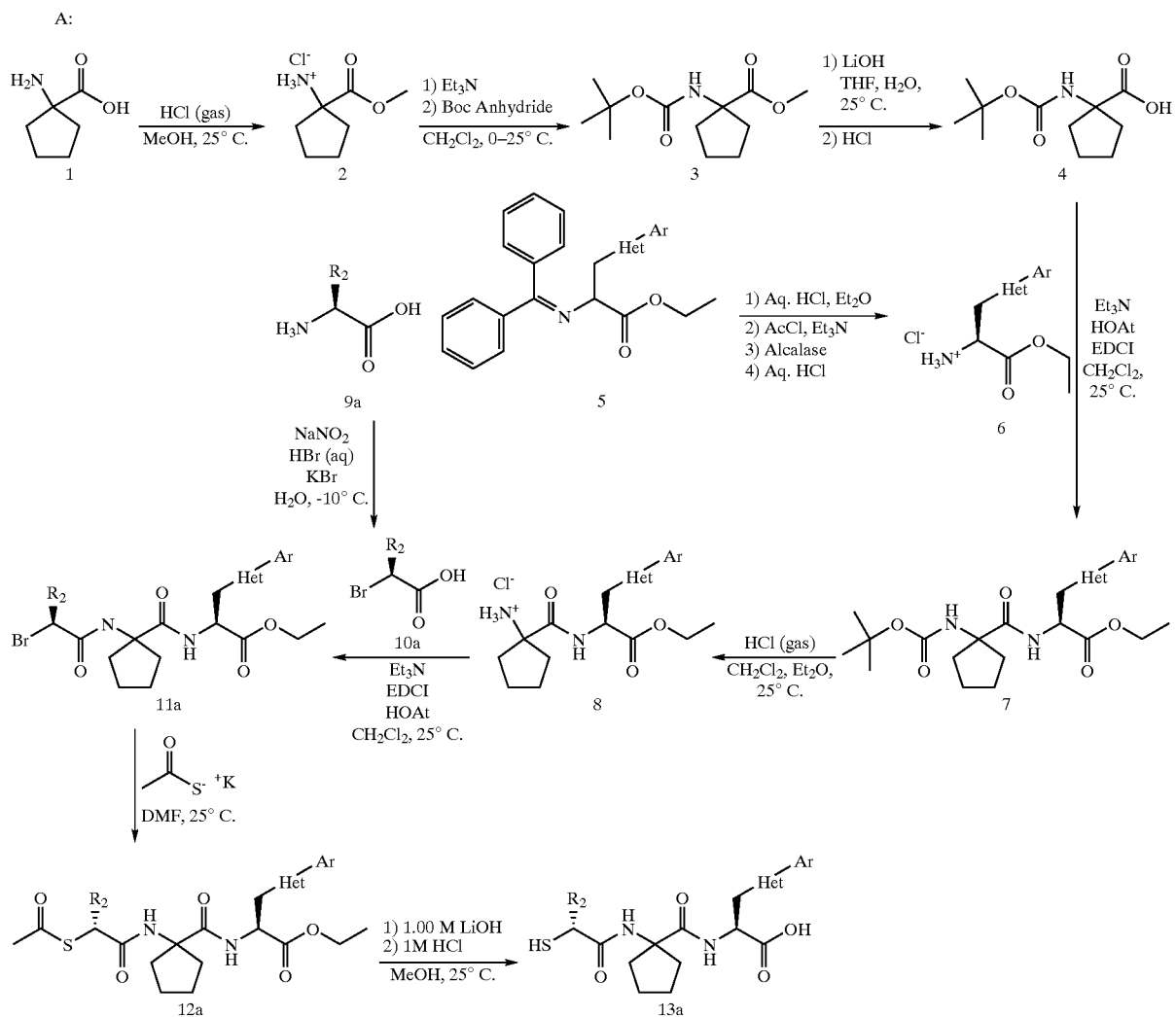

B: Alternatively, e.g. as illustrated for compounds wherein Het is 3-pyridyl, the amino acid intermediates are synthesized via palladium-catalyzed couplings of organoboron reagents or organostannanes (or organozinc compounds) with e.g. 2-benzhydrilydeneamino-3-(6-bromo-pyridin-3-yl)-propionic acid ethyl ester 14. The rest of the synthesis of the α-thiols is then completed as described in Sequence A.

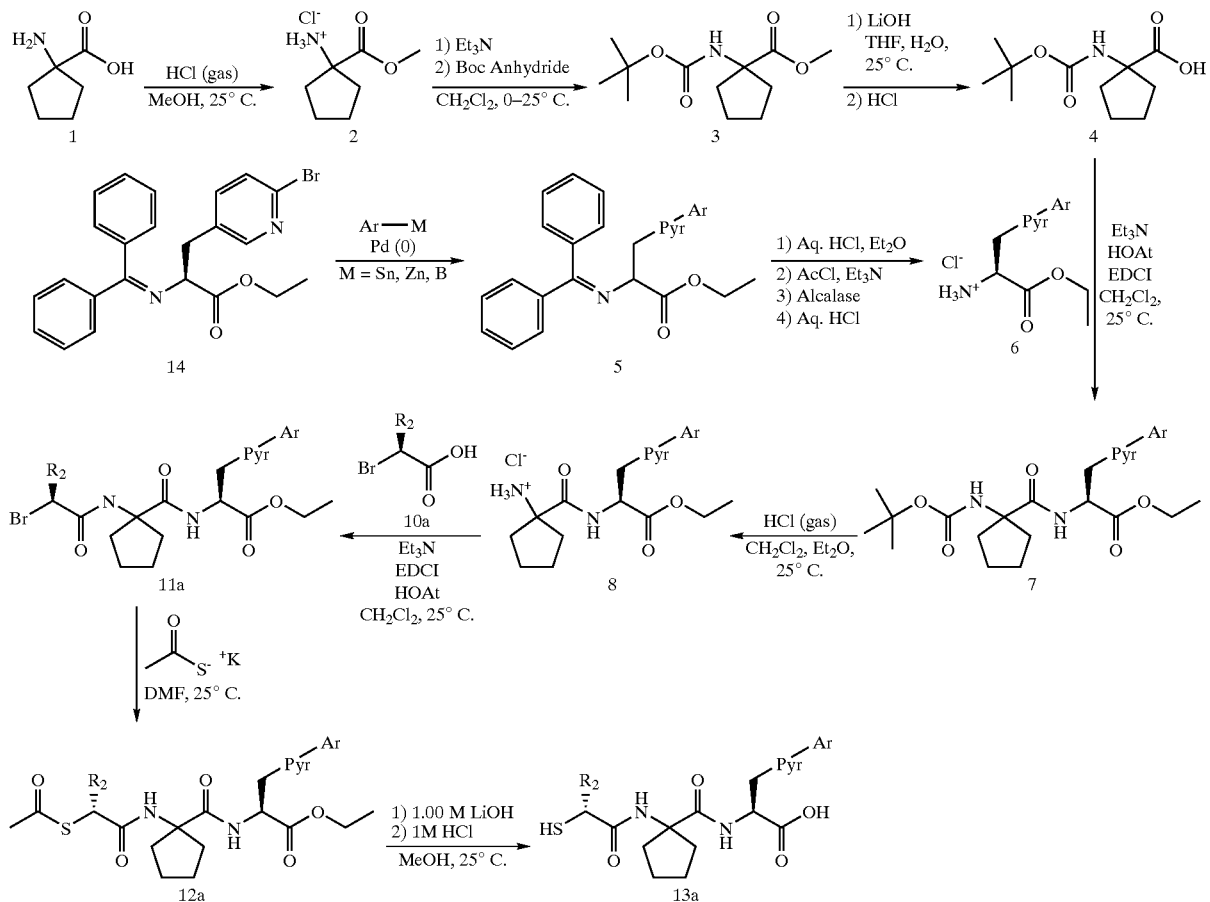

C: Alternatively, 3-(6-bromo-pyridin-3-yl)-2-[(1-tert-butoxycarbonylamino-cyclopentanecarbonyl)-amino]-propionic acid ethyl ester 15 (prepared according to Sequence A) is used as the intermediate for Suzuki coupling reactions to introduce the Ar group. The synthesis of the thiols is then continued as in Sequence A.

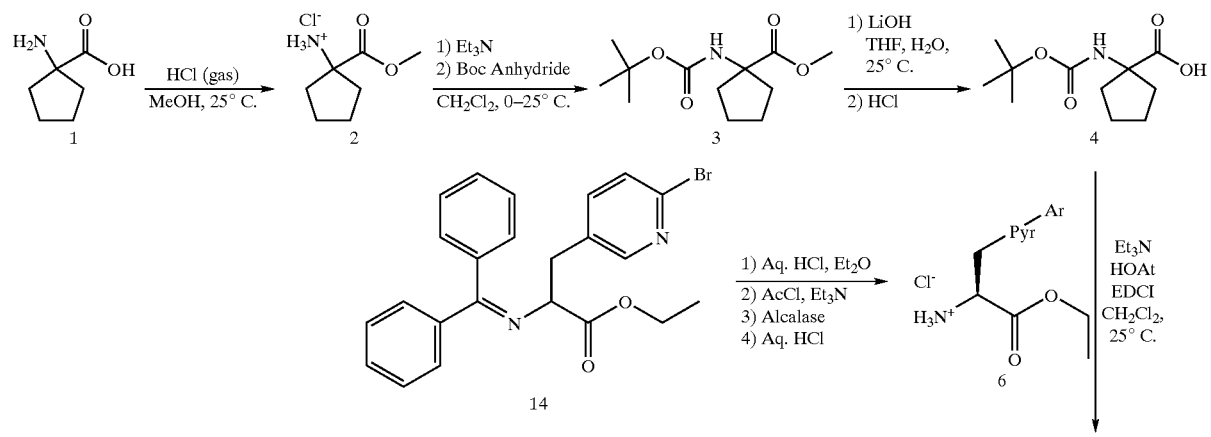

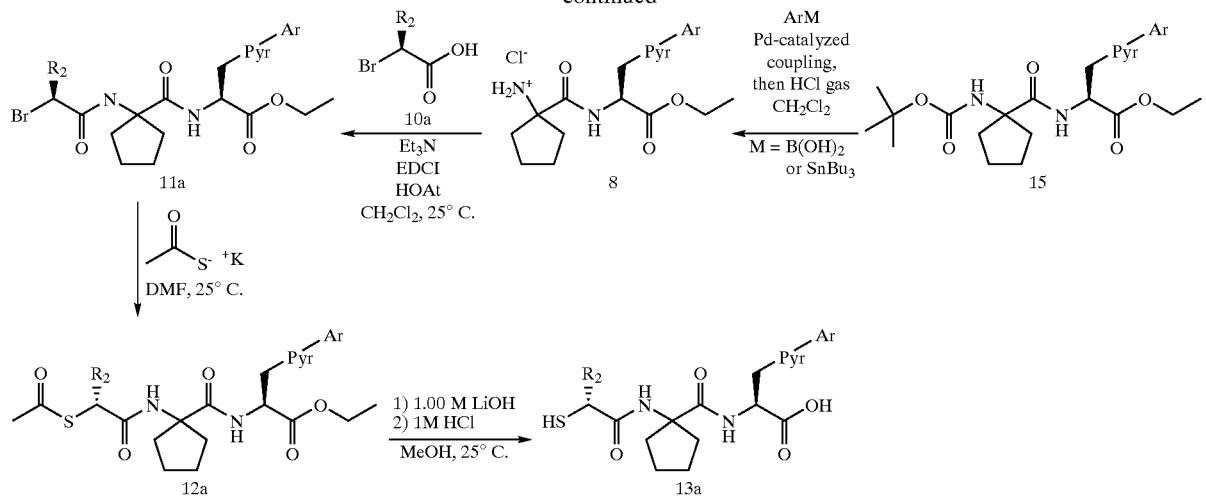

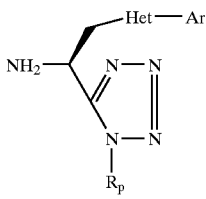

The compounds of the invention wherein Y represents 1H-5-tetrazolyl are similarly prepared, but starting with a tetrazole derivative of formula X'

(X')

wherein $R_p$ is a tetrazolyl protecting group (such as 2-cyanoethyl).

The tetrazole starting materials of formula X' are prepared from the corresponding N-acyl amino acids by first converting such to the N—$R_p$-substituted amides. The resulting amides are then treated under conditions known in the art for tetrazole ring formation, e.g. under conditions described in Tetrahedron Letters 1979, 491 and J. Org. Chem. 56, 2395 (1991), e.g. with trimethylsilyl azide in the presence of diisopropyl azodicarboxylate and triphenylphosphine. Removal of the N- acyl group leads to the starting materials of formula X'.

In the above illustrated sequence of reactions for process (c) the tetrazole protecting group is preferably removed after formation of the bromo intermediate and prior to reaction with e.g. potassium thioacetate.

Certain compounds of the invention and intermediates can be converted to each other according to general reactions well known in the art.

The free mercaptans may be converted to the S-acyl derivatives by reaction with a reactive derivative of a carboxylic acid (corresponding to $R_1$ being acyl in formula 1), such as an acid anhydride or said chloride, preferably in the presence of cobalt chloride ($COCl_2$) in an inert solvent such as acetonitrile or methylene chloride.

The free mercaptans, wherein $R_1$ represents hydrogen, may be oxidized to the corresponding disulfides, e.g. by air oxidation or with the use of mild oxidizing agents such as iodine in alcoholic solution. Conversely, disulfides may be reduced to the corresponding mercaptans, e.g. with reducing agents such as sodium borohydride, zinc and acetic acid or tributylphosphine.

Carboxylic acid esters may be prepared from a carboxylic acid by condensation with e.g. the halide corresponding to the esterifying alcohol in the presence of a base, or with an excess of the alcohol, in the presence of an acid catalyst, according to methods well-known in the art.

Carboxylic acid esters and S-acyl derivatives may be hydrolyzed, e.g. with aqueous alkali such as alkali metal carbonates or hydroxides.

Carbocyclic or heterocyclic aromatic compounds or intermediates may be reduced to the corresponding alicyclic compounds or interemediates according to methods illustrated herein, e.g. by catalytic hydrogenation.

In case mixtures of stereoisomers (e.g. diastereomers) are obtained, these can be separated by known procedures such as fractional crystallization and chromatography (e.g. thin layer, column, flash chromatography). Racemic free acids can be resolved into the optical antipodes by fractional crystallization of d- or l- (α-methylbenzylamine, cinchonidine, cinchonine, quinine, quinidine, dehydroabietylamine, brucine or strychnine) salts and the like. Racemic products, if not diastereoisomers, can first be converted to diastereoisomers with optically active reagents (such as optically active alcohols to form esters) which can then be separated as described above, and e.g. hydrolyzed to the individual enantiomer. Racemic products can also be resolved by chiral chromatography, e.g. high pressure liquid chromatography using a chiral adsorbent; also by enzymatic resolution, e.g. of esters with alcalase.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, for inhibiting endothelin converting enzyme, and e.g. for the treatment of endothelin dependent disorders such as those mentioned hereinabove, e.g. cardiovascular disorders such as hypertension, heart-failure, acute and chronic renal failure, stroke, and cerebral vasospasm, as well as asthma, erectile dysfunction and complications associated with transplantation.

The present invention also relates to the use of the compounds of the invention for the preparation of pharmaceutical compositions, especially pharmaceutical compositions having endothelin converting enzyme inhibiting activity.

The pharmaceutical compositions according to the invention are those suitable for enteral, such as oral or rectal, transdermal and parenteral administration to mammals, including man, for the treatment of endothelin dependent disorders, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 1 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereof. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) or other wavelengths as specified in the examples.

The prefixes R and S are used to indicate the absolute configuration at each asymmetric center. L-Amino acids as used herein correspond to the S-configuration. The stereochemical configuration, as assigned to the products of the examples, is indicated in a conventional manner in the respective structural formulae.

Abbreviations used are those standard in the art, e.g. "BOP" reagent is the abbreviation for benzotriazol-1-yloxy-tris (dimethylamino) phosphonium hexafluorophosphate, HOAT is the abbreviation for 1-hydroxy-7-azabenzotriazole, HOBT is the abbreviation for 1-hydroxybenzotriazole, EDCI is the abbreviation for 1-ethyl-3-(3-dimethylaminopropyl) carbodiimide hydrochloride, DCC is the abbreviation for dicyclohexylcarbodiimide.

EXAMPLES

Preparation of α-bromocarboxylic acids (a) 5.00 g (38.1 mmol) of L-Norleucine (αS-aminohexanoic acid) and 22.7 g (191 mmol) of potassium bromide are dissolved in 50 mL of water at room temperature. Then, 10.8 mL (95.5 mmol) of aqueous 48% hydrobromic acid is added and the mixture is cooled to −12° C. in an ice/NaCl bath. Next, the flask is equipped with an addition funnel containing 3.16 g (45.7 mmol) of sodium nitrite dissolved in 20 mL of water. The sodium nitrite solution is allowed to drip into the reaction mixture over the course of 30 minutes. After the addition of sodium nitrite is complete, the mixture is stirred for an additional 45 minutes, transferred to a separatory funnel, and diluted with ethyl acetate. The layers are separated and the aqueous phase is extracted two times with ethyl acetate. The combined ethyl acetate phases are washed three times with aqueous saturated sodium bisulfite (removing the yellow color), dried over sodium sulfate, and evaporated to dryness to afford a clear colorless oil. Further drying under high vacuum yields α-S-bromo- hexanoic acid. $^1$H NMR (250 MHz, CDCl$_3$) δ10.4 (s, 1H), 4.24 (t, 1H), 1.92–2.17 (m, 2H), 1.32–1.55 (m, 4H, 0.93 (t, 3H).

Similarly prepared are:

(b) αR-bromohexanoic acid; $^1$H NMR (250 MHz, CDCl$_3$) δ9.80 (s, 1H), 4.24 (t, 1H), 1.81–2.26 (m, 2H), 1.32–1.55 (m, 4H), 0.93 (t, 3H).

(c) αS-bromo-βR-methylpentanoic acid; $^1$H NMR (250 MHz, CDCl$_3$) δ10.88 (s, 1H), 4.29 (d, 1H), 1.86–2.09 (m, 0.5H), 1.43–1.68 (m, 0.5H), 1.24–1.43 (m, 2H), 1.07 (d, 3H), 0.95 (t, 3H).

(d) αS-bromo-βS-methylpentanoic acid; $^1$H NMR (250 MHz, CDCl$_3$) δ10.35 (s, 1H), 4.12 (d, 1H), 1.98–2.10 (m, 0.5H), 1.67–1.83 (m, 0.5H), 1.24–1.48 (m, 2H), 1.05 (d, 3H), 0.92 (t, 3H).

(e) αR-bromo-βR-methylpentanoic acid; $^1$H NMR (300 MHz, CDCl$_3$) δ10.65 (s, 1H), 4.11 (d, 1H), 1.99–2.10 (m, 0.5H), 1.67–1.80 (m, 0.5H), 1.22–1.44 (m, 2H), 1.04 (d, 3H), 0.91 (t, 3H).

(f) αR-bromo-βS-methylpentanoic acid; $^1$H NMR (300 MHz, CDCl$_3$) δ10.15 (s, 1H), 4.27 (d, 1H), 1.90–2.06 (m, 0.5H), 1.43–1.54 (m, 0.5H), 1.22–1.38 (m, 2H), 1.03 (d, 3H), 0.93 (t, 3H).

(g) αR-bromo-γ-methylpentanoic acid; $^1$H NMR (250 MHz, CDCl$_3$) δ9.81 (s, 1H), 4.29 (d, 1H), 1.92 (t, 2H), 1.72–1.89 (m, 1H), 0.97 (d, 3H), 0.92 (d, 3H).

(h) αS-bromo-γ-methylpentanoic acid; $^1$H NMR (250 MHz, CDCl$_3$) δ9.94 (s, 1H), 4.35 (d, 1H), 1.94 (t, 2H), 1.69–1.93 (m, 1H), 0.94 (d, 3H), 0.89 (d, 3H).

(i) αR-bromo-γ-thiomethylbutanoic acid; $^1$H NMR (250 MHz, CDCl$_3$) δ9.56 (s, 1H), 4.50 (dd, 1H), 2.57–2.76 (m, 2H), 2.22–2.43 (m, 2H), 2.11 (s, 3H).

(j) αS-bromo-γ-thiomethylbutanoic acid; $^1$H NMR (250 MHz, CDCl$_3$) δ10.18 (s, 1H), 4.50 (dd, 1H), 2.56–2.76 (m, 2H), 2.20–2.43 (m, 2H), 2.11 (s, 3H).

(k) αR-bromopentanoic acid; $^1$H NMR (250 MHz, CDCl$_3$) δ10.06 (s, 1H), 4.25 (dd, 1H), 1.91–2.15 (m, 2H), 1.34–1.62 (m, 2H), 0.97 (t, 3H).

(l) αS-bromopentanoic acid; $^1$H NMR (250 MHz, CDCl$_3$) δ10.70 (s, 1H), 4.25 (dd, 1H), 1.93–2.14 (m, 2H), 1.34–1.62 (m, 2H), 0.96 (t, 3H).

(m) αR-bromo-βR-methoxybutanoic acid; $^1$H NMR (300 MHz, CDCl$_3$) δ8.62 (s, 1H), 4.35 (d, 1H), 4.77 (q, 1H), 3.43 (s, 3H), 1.32 (d, 3H).

(n) αR-bromopropanoic acid; $^1$H NMR (250 MHz, CDCl$_3$) δ9.76 (s, 1H), 4.40 (q, 1H), 1.85 (d, 3H).

(o) αR-bromo-βS-hydroxybutanoic acid; $^1$H NMR (300 MHz, CDCl$_3$) δ6.60 (br s, 2H), 4.28 (d, 1H), 4.13–4.21 (m, 1H), 1.33 (d, 3H).

(p) αS-bromo-βR-hydroxybutanoic acid; $^1$H NMR (300 MHz, CDCl$_3$) δ6.66 (br s, 2H), 4.29 (d, 1H), 4.10–4.21 (m, 1H), 1.34 (d, 3H).

(q) α-bromo-p-phenyl-propionic acid 10; $^1$H NMR (250 MHz, CDCl$_3$) δ7.25 (m, 5H), 4.40 (t, 1H), 3.45 (dd, 1H), 3.25 (dd, 1H); IR (CH$_2$Cl$_2$, cm$^{-1}$) 1755, 1722, 1603, 1495.

(r) α-bromo-β-naphthalen-2-yl-propionic acid; $^1$H NMR (250 MHz, CDCl$_3$) δ7.50–7.90 (m, 4H), 7.25–7.50 (m, 3H), 4.50 (t, 1H), 3.55–3.65 (m, 1H), 3.25–3.45 (m, 1H); IR (CH$_2$Cl$_2$, cm$^{-1}$) 1752, 1720, 1599, 1510, 1147, 822. $[\alpha]_D$+12.146 (10.55 mg/mL in CH$_2$Cl$_2$).

(s) β-biphenyl-4-yl-α-bromopropionic acid; $^1$H NMR (250 MHz, CDCl$_3$) δ7.20–7.60 (m, 9H), 4.45 (t, 1H), 3.50 (dd, 1H), 3.25 (dd, 1H).

(t) α-bromo-β-cyclohexyl-propionic acid; White solid; $^1$H NMR (250 MHz, CDCl$_3$) δ9.24 (s, 1H), 4.01 (s, 1H), 2.03–2.10 (m, 1H), 1.50–1.95 (m, 5H), 0.94–1.36 (m, 5H); IR (KBr, cm$^{-1}$) 1753, 1716, 1112. [α]D+36.104 (10.1 mg/mL in CH$_2$Cl$_2$).

(u) β-(4-benzyloxycarbonyloxy-phenyl)-α-bromopropionic acid; $^1$H NMR (300 MHz, CDCl$_3$) δ7.38–7.43 (m, 5H), 7.27 (d, 2H), 7.14 (d, 2H), 5.27 (s, 2H), 4.40 (dd, 1H), 3.45 (dd, 1H); R$_f$ 0.35 (EtOAc: hexane: AcOH 50:50:1).

Example 1

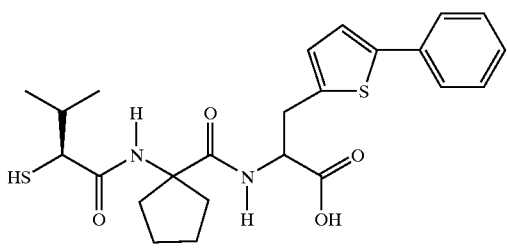

(a)

2-{[1-(2-Mercapto-3-methyl-butanoylamino)-cyclopentanecarbonyl]-amino}-3-(5-phenyl-thien-2-yl)-propionic Acid 55 mg (0.101 mmol) of 2-{[1-(2-Acetylthio-3-methyl-butanoylamino)-cyclopentanecarbonyl]-amino}-3-(5-phenyl-thien-2-yl)-propionic acid ethyl ester is dissolved in 2 mL of MeOH. 0.41 mL of 1N NaOH is added, and the solution is stirred at room temperature for 3 h. The reaction mixture is diluted with water, and MeOH is removed in vacuo. The residue is partitioned between water and Et$_2$O. The aqueous phase is extracted twice with Et$_2$O, acidified with 0.41 mL of 1N HCl, and then extracted with EtOAc. The EtOAc phase is concentrated to furnish the product; mp 154–155° C.

The preparation of the starting material involves the following intermediates:

(1) 2-Benzhydrilydene-amino-3-(5-phenyl-thien-2-yl)-propionic acid ethyl ester Prepared according to the procedure reported by Stork et al (*J. Org. Chem.* 1976, 3491) for the synthesis of amino esters, using NaHMDS as the base, from 2-bromomethyl-5-phenyl-thiophene; $^1$H NMR (300 MHz, CDCl$_3$) δ7.64 (dd, 2H), 7.50 (dd, 2H), 7.20–7.40 (m, 9H), 7.08 (d, 1H), 6.86 (br d, 2H), 6.71 (d, 1H), 4.15–4.31 (m, 3H), 3.40–3.48 (m, 2H), 1.28 (t, 3H).

(2) 2-Amino-3-(5-phenyl-thien-2-yl)-propionic acid ethyl ester hydrochloride 527 mg (1.20 mmol) of 2-Benzhydrylidene-amino-3-(5-phenyl-thien-2-yl)-propionic acid ethyl ester and 13 mL (13 mmol) of 1N HCl are dissolved in 10 mL of Et$_2$O, and the solution is stirred at room temperature for 18 h. The reaction mixture is partitioned between water and ether. The aqueous phase is separated and extracted twice with ether, and then concentrated. The residue is dried under vacuum at 65° C. to obtain the product as a white solid. $^1$H NMR (300 MHz, CD$_3$OD) δ7.58 (d, 2H), 7.37 (t, 1H), 7.28–7.32 (m, 1H), 7.10–7.25 (m, 2H), 6.96 (d, 1H), 4.30–4.37 (m, 3H), 3.48 (d, 2H), 1.33 (t, 3H).

(3)

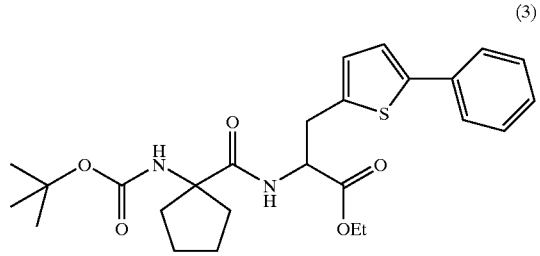

2-[(1-tert-Butoxycarbonylamino-cyclopentanecarbonyl)-amino]-3-(5-phenyl-thien-2-yl)-propionic acid ethyl ester 276 mg (0.885 mmol) of 2-Amino-3-(5-phenyl-thien-2-yl)-propionic acid ethyl ester hydrochloride, 203 mg (0.885 mmol) of N-Boc-cycloleucine, 0.12 mL (0.885 mmol) of Et$_3$N, 120 mg (0.885 mmol) of HOBT, and 201 mg (0.974 mmol) of DCC are suspended in 10 mL of CH$_2$Cl$_2$, and the solution is stirred at room temperature for 72 h. The reaction mixture is filtered, taken up in EtOAc, filtered again, and partitioned between EtOAc and water. The organic phase is washed with aqueous saturated NaHCO$_3$ solution, brine, dried over MgSO$_4$, filtered, and then concentrated. The residue is purified by chromatography on silica gel (25% EtOAc/hexane, R$_f$ 0.4) to yield the product as a solid. $^1$H NMR (250 MHz, CDCl$_3$) δ7.50 (dd, 2H), 7.35 (dt, 2H), 7.22–7.28 (m, 1H), 7.10 (d, 1H), 6.76 (d, 1H), 4.75–4.85 (m, 2H), 4.19 (q, 2H), 3.36 (d, 2H), 2.15–2.35 (m, 2H), 1.65–1.95 (m, 6H), 1.39 (s, 9H), 1.26 (t, 3H).

(4) 2-[(1-Amino-cyclopentanecarbonyl)-amino]-3-(5-phenyl-thien-2-yl)-propionic acid ethyl ester hydrochloride HCl gas is bubbled vigorously into a solution of 158 mg (0.325 mmol) of 2-[(1-tert-butoxycarbonylaminocyclopentanecarbonyl)-amino]-3-(5-phenyl-thien-2-yl)-propionic acid ethyl ester in 5 mL of CH$_2$Cl$_2$ at 0° C., and the solution is warmed to room temperature and stirred for 12 h. The reaction mixture is then concentrated in vacuo to produce the product as a pale yellow solid. $^1$H NMR (250 MHz, CD$_3$OD) δ7.50 (dd, 2H), 7.35 (dt, 2H), 7.23 (br d, 1H), 7.20 (d, 1H), 6.88 (d, 1H), 4.70 (dd, 1H), 4.21 (q, 2H), 3.50 (dd, 1H), 3.30 (dd, 1H), 2.15–2.35 (m, 2H), 1.80–2.10 (m, 6H), 1.28 (t, 3H).

(5)

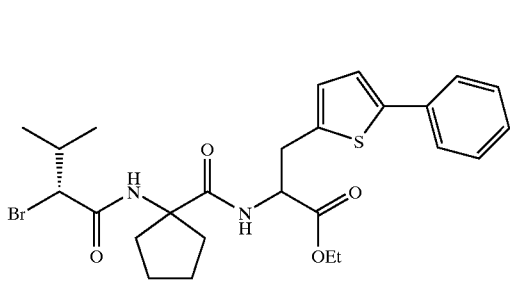

2-{[2-Bromo-3-methyl-butanoylamino-)-cyclopentanecarbonyl]-amino}-3-(5-phenyl-thien-2-yl)-propionic acid ethyl ester 100 mg (0.236 mmol) of 2-[(1-Amino-cyclopentanecarbonyl)-amino]-3-(5-phenyl-thien-2-yl)-propionic acid ethyl ester hydrochloride, 67 mg (0.236 mmol) of 2-bromo-3-methyl-butanoic acid diisopropylamine salt, 32 mg (0.236 mmol) of HOAT, and 59 mg (0.284 mmol) of DCC are suspended in 3 mL of CH$_2$Cl$_2$, and the solution is stirred at room temperature for 18 h. The reaction mixture is filtered, taken up in EtOAc, filtered again, and partitioned between EtOAc and water. The organic phase is washed with aqueous saturated NaHCO$_3$ solution, brine, dried over MgSO$_4$, filtered, and then concentrated. The residue is purified by chromatography on silica gel (30% EtOAc/hexane, R$_f$ 0.3) to obtain a solid. $^1$H NMR (300 MHz, CDCl$_3$) δ7.50 (d, 2H), 7.35 (t, 2H), 7.22–7.32 (m, 1H), 7.15 (d, 1H), 6.76 (dd, 1H), 4.75–4.85 (m, 1H), 4.02–4.25 (m, 3H), 3.30–3.50 (ABX m, 2H), 2.20–2.40 (m, 3H), 1.85–2.15 (m, 2H), 1.60–1.80 (m, 4H), 1.26 (t, 3H), 0.98 (dd, 3H), 0.94 (dd, 3H).

(6)

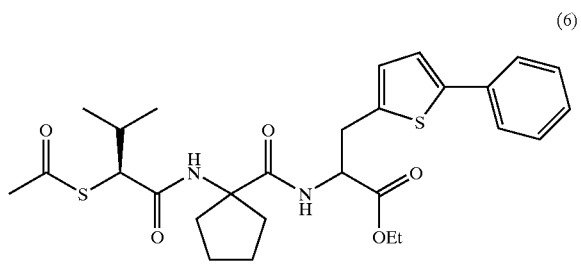

2-{[1-(2-Acetylthio-3-methyl-butanoylamino-)-cyclopentanecarbonyl]-amino}-3-(5-phenyl-thien-2-yl)-propionic acid ethyl ester. Thioacetic acid (14 mL, 0.197 mmol), is added to a suspension of 72 mg (0.131 mmol) of 2-{[2-bromo-3-methyl-butanoylamino-)-cyclopentanecarbonyl]-amino}-3-(5-phenyl-thien-2-yl)-propionic acid ethyl ester and 34 mg (0.249 mmol) of potassium carbonate in 1.5 mL of THF, and the solution is stirred at room temperature for 18 h. The reaction mixture is partitioned between EtOAc and water. The organic phase is washed with aqueous saturated NaHCO$_3$ solution, brine, dried over MgSO$_4$, filtered, and then concentrated. The residue is purified by chromatography on silica gel (30% EtOAc/hexane, R$_f$ 0.3) to obtain a solid. $^1$H NMR (250 MHz, CDCl$_3$) δ7.55 (br d, 2H), 7.30 (br t, 2H), 7.20 (app t, 1H), 7.10 (app t, 1H), 6.80 (d, 1H), 6.35 (br d, 1H), 4.70–4.80 (m, 1H), 4.15 (q, 2H), 3.65 (dd, 1H), 3.20–3.40 (ABX m, 2H), 2.30, 2.28 (s each, total 3H), 2.10–2.40 (m, 3H), 1.80–2.05 (m, 2H), 1.60–1.80 (m, 4H), 1.26 (dt, 3H), 1.00 (dd, 6H).

Similarly prepared are:

(b)

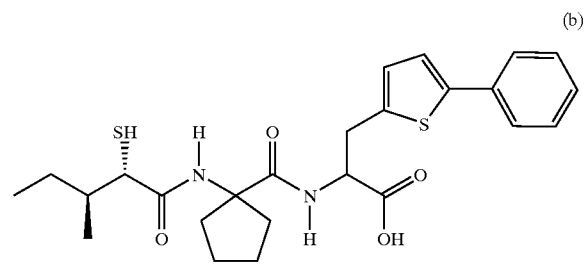

2-{[1-(2-Mercapto-3-methyl-pentanoylamino)-cyclopentanecarbonyl]-amino}-3-(5-phenyl-thien-2-yl)-propionic acid; mp 131–133° C.

(c)

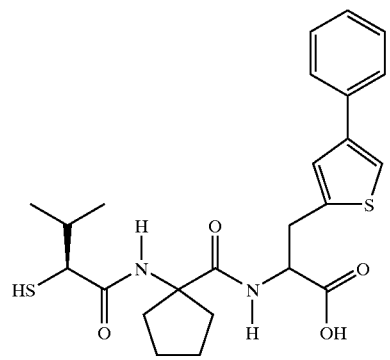

2-{[1-(2-Mercapto-3-methyl-butanoyllamino)-cyclopentanecarbonyl]-amino}-3-(4-phenyl-thien-2-yl)-propionic acid; mp 158–164° C. The starting material, 2-benzhydrilydene-amino-3-(4-phenyl-thien-2-yl)-propionic acid ethyl ester is prepared according to the procedure reported by Stork et al (*J. Org. Chem.* 1976, 3491) for the synthesis of amino esters, using NaHMDS as the base, from 2-bromomethyl-4-phenyl-thiophene. $^1$H NMR (250 MHz, CDCl$_3$) δ7.58–7.64 (two d, 2H), 7.20–7.40 (m, 11H), 7.14 (s, 1H), 6.94 (s, 1H), 6.75 (br d, 2H), 4.06–4.26 (m, 3H), 3.30–3.48 (m, 2H), 1.19 (T, 3H).

(d)

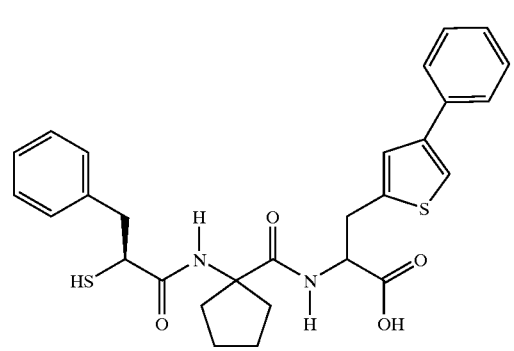

2-{[1-(2-Mercapto-3-phenyl-propionylamino)-cyclopentanecarbonyl]-amino}-3-(4-phenyl-thien-2-yl)-propionic acid; mp 133–136° C.

(e)

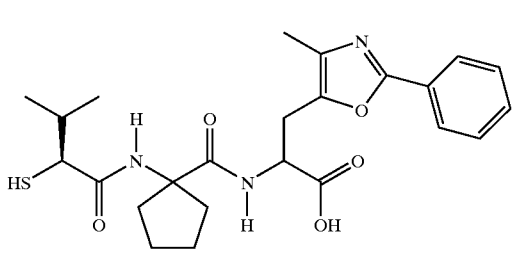

2-{[1-(2-Mercapto-3-methyl-butanoylamino)-cyclopentanecarbonyl]-amino}-3-(4-methyl-2-phenyl-oxazol-5-yl)-propionic acid; mp 227–229° C.

The starting material is prepared as follows:

19.0 mL of 1.0M DIBAL-H solution in toluene is added slowly to a solution of 1.63 g (7.5 mmol) of 4-methyl-2-phenyl-oxazole-5-carboxylic acid methyl ester (*J. Chem. Soc., Chem. Comm.* 1995, 22, 2335) in 30 mL of THF at −78° C. The cooling bath is removed, and the reaction mixture is stirred overnight. The reaction mixture is cooled to −78° C. and quenched with 9 mL of MeOH. The cooling bath is removed, and 9 mL of brine and 6.5 g of $Na_2SO_4$ are added, and the reaction mixture is stirred vigorously for 2 h, and then filtered off, and concentrated in vacuo to produce (4-methyl-2-phenyl-oxazol-5-yl)-methanol as a solid; $^1$H NMR (250 MHz, $CDCl_3$) δ7.93–8.01 (m, 2H), 7.37–7.43 (m, 3H), 4.65 (s, 2H), 2.61 (br s, 1H), 2.18 (s, 3H).

80 mL (0.67 mmol) of $PBr_3$ is added slowly to a solution of 104 mg (0.57 mmol) of (4-methyl-2-phenyl-oxazol-5-yl)-methanol in 0.5 mL of $Et_2O$ and 1.5 mL of $CH_2Cl_2$ at 0° C. The cooling bath is removed, and the reaction mixture is stirred for 4 h. The reaction mixture is then partitioned between saturated aqueous $NaHCO_3$ solution and $Et_2O$. The organic phase is separated and washed with brine, dried over $MgSO_4$, filtered, and concentrated in vacuo to produce 5-bromomethyl-4-methyl-2-phenyl-oxazole as a solid; $^1$H NMR (250 MHz, $CDCl_3$) δ7.90–7.99 (m, 2H), 7.32–7.40 (m, 3H), 4.50 (s, 2H), 2.16 (s, 3H).

2-Benzhydrilydene-amino-3-(4-methyl-2-phenyl-oxazol-5-yl)-propionic acid ethyl ester is prepared according to the procedure reported by Stork et al (*J. Org. Chem.* 1976, 3491) for the synthesis of amino esters, using NaHMDS as the base, from 5-bromomethyl-4-methyl-2-phenyl-oxazole; $^1$H NMR (300 MHz, $CDCl_3$) δ7.79 (dd, 2H), 7.54–7.60 (m, 3H), 7.22–7.51 (m, 6H), 7.14 (app t, 2H), 6.78 (br d, 2H), 4.40 (dd, 1H), 4.16–4.32 (m, 2H), 3.25–3.28 (m, 2H), 2.10 (s, 3H), 1.29 (t, 3H).

(f)

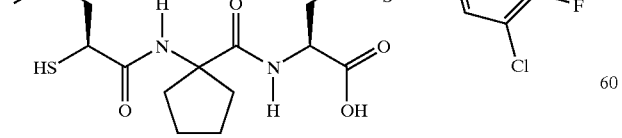

3-[2-(3-Chloro-4-fluoro-phenyl)-thiazol-5-yl]-2-{[1-(2-mercapto-4-methyl-pentanoylamino)-cyclopentanecarbonyl]-amino}-propionic acid; mp 96–98° C.

The starting material, the enantiomer of 2-amino-3-[2-(3-chloro-4-fluorophenyl)-thiazol-5-yl]-propionic acid ethyl ester is prepared via resolution of 2-(N-acetylamino)-3-[2-(3-chloro-4-fluorophenyl)-thiazol-5-yl]-propionic acid ethyl ester with alcalase to the optically active N-acetyl amino acid according to the procedure described e.g. in Canadian J. of Chemistry 68, 960 (1990) and Indian J. Chemistry Sect. B 1992, 31B, 851–854, followed by conversion to the amino acid ethyl ester.

(g)

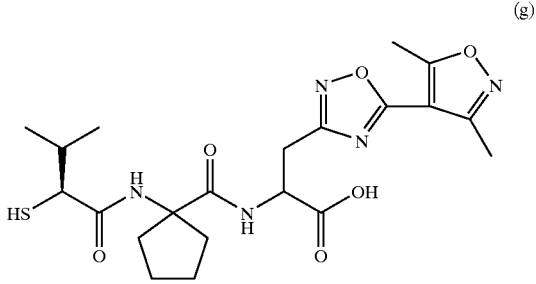

3-[5-(3,5-Dimethyl-isoxazol-4-yl)-[1,2,4]oxadiazol-3-yl]-2-{[1-(2-mercapto-3-methyl-butanoylamino)-cyclopentanecarbonyl]-amino}-propionic acid; mp 170–172° C.

The starting material, 2-benzhydrilydene-amino-3-[5-(3,5-dimethyl-isoxazol-4-yl)-[1,2,4]oxadiazol-3-yl]-propionic acid ethyl ester is prepared according to the procedure reported by Stork et al (*J. Org. Chem.* 1976, 3491) for the synthesis of amino esters, using NaHMDS as base, from 3-chloromethyl-5-(3,5-dimethyl-isoxazol-4-yl)-[1,2,4]oxadiazole. $^1$H NMR (300 MHz, $CDCl_3$) δ7.62 (d, 2H), 7.30–7.48 (m, 6H), 7.54 (d, 2H), 7.09 (d, 2H), 4.68 (app t, 1H), 4.20 (q, 2H), 3.40–3.50 (ABX m, 2H), 2.68 (s, 3H), 2.47 (s, 3H), 1.31 (t, 3H).

(h)

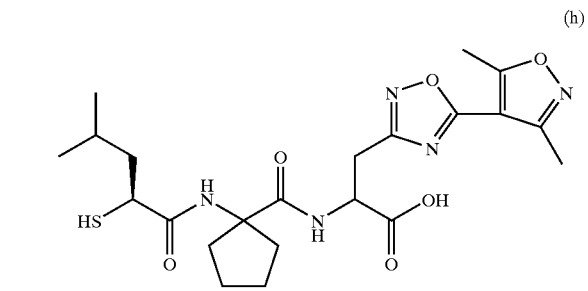

3-[5-(3,5-Dimethyl-isoxazol-4-yl)-[1,2,4]oxadiazol-3-yl]-2-{[1-(2-mercapto-4-methyl-pentanoylamino)-cyclopentanecarbonyl]-amino}-propionic acid; mp 151–153° C.

Example 2

(a)

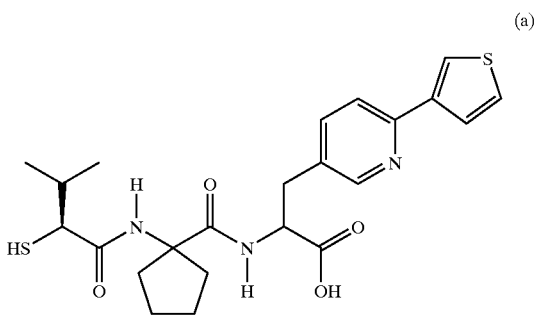

2-{[1-(2-Mercapto-3-methyl-butanoylamino)-cyclopentanecarbonyl]-amino}-3-[6-(thien-3-yl)-pyridin-3- yl]-propionic acid is prepared similarly to procedure of example 1 from 2-benzhydrilydene-amino-3-[6-(thien-3-yl)-pyridin-3-yl]-propionic acid ethyl ester which is in turn prepared via palladium catalyzel coupling of thiophene-3-boronic acid with 2-benzhydrilydene-amino-3-(6-bromo-pyridin-3-yl)-propionic acid ethyl ester; mp 215–217° C.

The starting material is prepared as follows:

2-Benzhydrilydene-amino-3-(6-bromo-pyridin-3-yl)-propionic acid ethyl ester is prepared according to the procedure reported by Stork et al (*J. Org. Chem.* 1976, 3491) for the synthesis of amino esters, using NaHMDS as the base, from 2-bromo-5-bromomethyl-pyridine; $^1$H NMR (250 MHz, CDCl$_3$) δ7.99 (d, 1H), 7.48–7.60 (m, 3H), 7.05–7.40 (m, 8H), 6.12–6.22 (m, 2H), 4.00–4.15 (m, 3H), 3.04–3.10 (m, 2H), 1.15 (dt, 3H).

A suspension of thiophen-3-boronic acid (760 mg, 5.9 mmol), 2-benzhydrilydene-amino-3-(6-bromo-pyridin-3-yl)-propionic acid ethyl ester (2.0 g, 4.6 mmol), PdCl$_2$(dppf) (191 mg, 0.23 mmol), and K$_3$PO$_4$ (4.89 g, 23 mmol) in 32 mL of DME is heated at 85° C. for 18 h, and then cooled to room temperature. The reaction mixture is then partitioned between water and EtOAc. The organic phase is separated, and washed with brine, dried over MgSO$_4$, filtered, and concentrated. The residue is purified by chromatography on silica gel (25% EtOAc/hexane) to provide 2-benzhydrilydene-amino-3-[6-(thien-3-yl)-pyridin-3-yl]-propionic acid ethyl ester as a solid (88% yield); $^1$H NMR (250 MHz, CDCl$_3$) δ8.30 (d, 1H), 7.82 (dd, 1H), 7.56–7.60 (m, 2H), 7.22–7.47 (m, 10H), 6.72 (d, 2H), 4.25 (dd, 1H), 4.19 (dq, 2H), 3.13–3.31 (ABX m, 2H), 1.25 (t, 3H).

(b)

2-{[1-(2-Mercapto-3-methyl-pentanoylamino)-cyclopentanecarbonyl]-amino}-3-[6-(thien-3yl)-pyridin-3-yl]-propionic acid; mp 200–202° C.

(c)

2-{[1-(2-Mercapto-hexanoylamino)-cyclopentanecarbonyl]-amino}-3-[6-(thien-3-yl)-pyridin-3-yl]-propionic acid; mp 204–206° C.

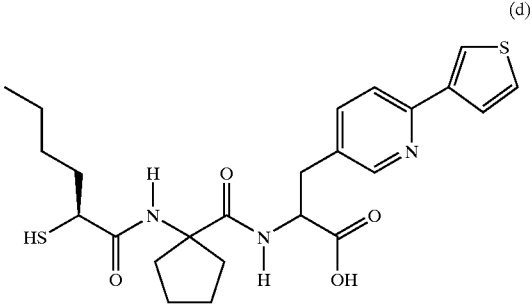

(d)

2-{[1-(2-Mercapto-hexanoylamino)-cyclopentanecarbonyl]-amino}-3-[6-(thien-3-yl)-pyridin-3-yl]-propionic acid; mp 205–207° C.

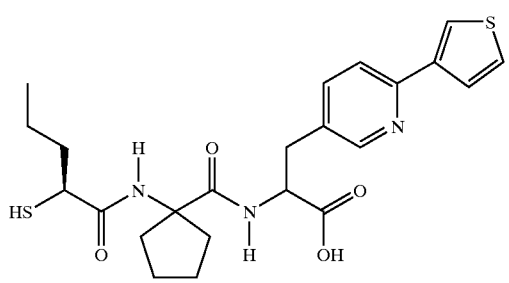

(e)

2-{[1-(2-Mercapto-hexanoylamino)-cyclopentanecarbonyl]-amino}-3-[6-(thien-3-yl)-pyridin-3-yl]-propionic acid; mp 186–188° C.

(f)

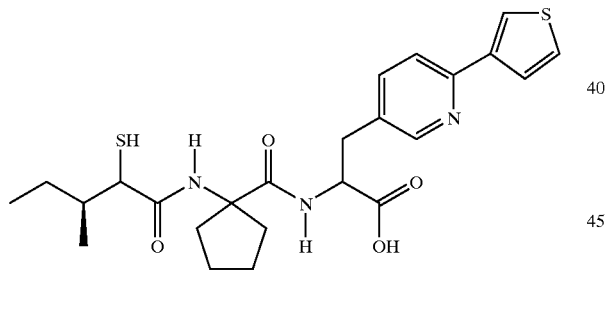

2-{[1-(2-Mercapto-4-methyl-pentanoylamino)-cyclopentanecarbonyl]-amino}-3-[6-(thien-3-yl)-pyridin-3-yl]-propionic acid; mp 204–205° C.

(g)

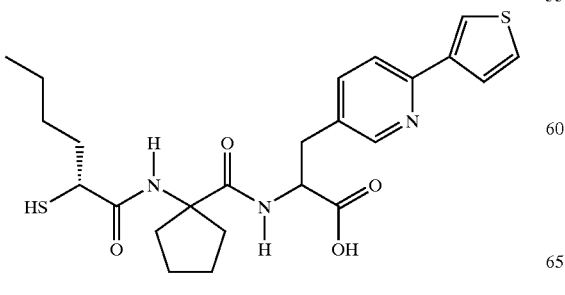

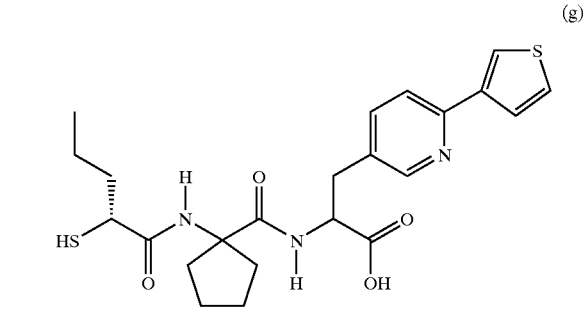

2-{[1-(2-Mercapto-pentanoylamino)-cyclopentanecarbonyl]-amino-}3-[6-(thien-3-yl)-pyridin-3-yl]-propionic acid; mp 202–205° C.

2-{[1-(2-Mercapto-4-methyl-pentanoylamino)-cyclopentanecarbonyl]-amino}-3-[6-(thien-3-yl)-pyridin-3-yl]-propionic acid; mp 216–219° C.

(h)

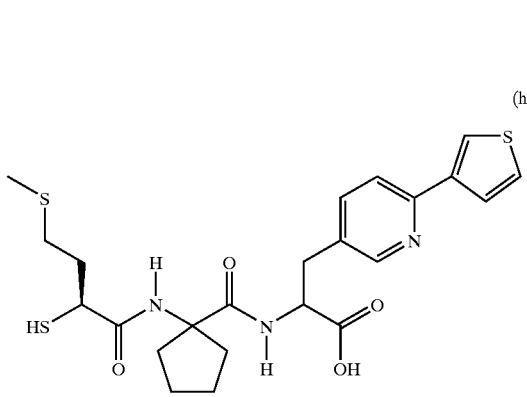

(k)

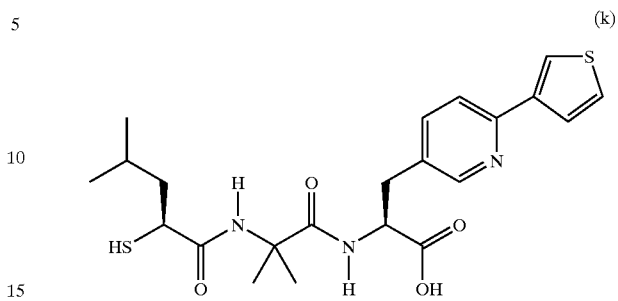

2-[2-(2-Mercapto-4-methyl-pentanoylamino)-2-methyl-propionylamino]-3-[6-(thien-3-yl)-pyridin-3-yl]-propionic acid; mp 218–220° C.

2-{[1-(2-Mercapto-4-methylthio-butanoylamino)-cyclopentanecarbonyl]-amino}-3-[6-(thien-3-yl)-pyridin-3-yl]-propionic acid; mp 197–199° C.

(l)

(i)

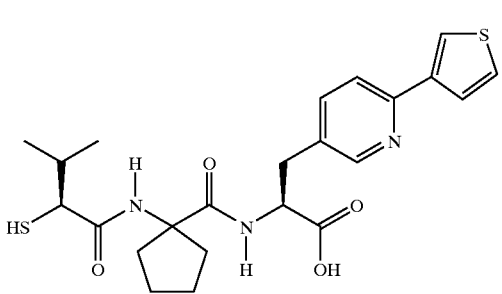

2-{[1-(2-Mercapto-3-phenyl-propionylamino)-cyclopentanecarbonyl]-amino}-3-[6-(thien-3-yl)-pyridin-3-yl]-propionic acid; mp 208–209° C.

(m)

2-{[1-(2-Mercapto-3-methyl-butanoylamino)-cyclopentanecarbonyl]-amino}-3-[6-(thien-3-yl)-pyridin-3-yl]-propionic acid; mp 170–172° C.

2-{[1-(3-Cyclohexyl-2-mercapto-propionylamino)-cyclopentanecarbonyl]-amino}-3-[6-(thien-3-yl)-pyridin-3-yl]-propionic acid; mp 215–216° C.

(j)

(n)

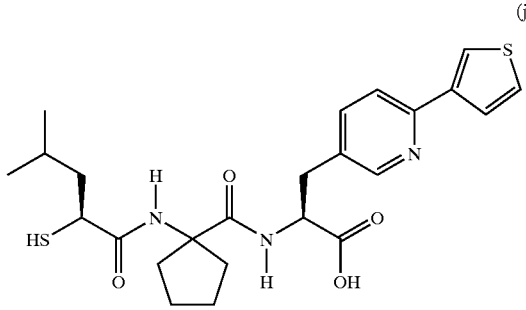

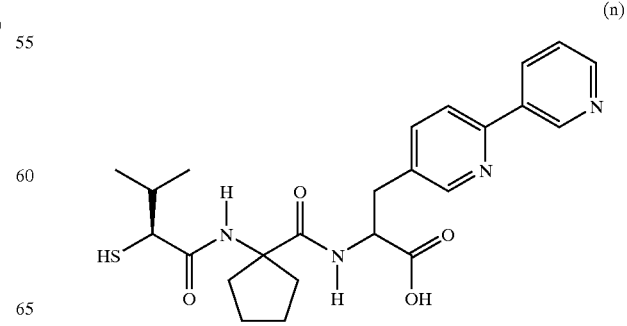

2-{[1-(2-Mercapto-3-methyl-butanoylamino)-cyclopentanecarbonyl]-amino}-3-[6-(pyridin-3-yl)-pyridin-3-yl]-propanoic acid; mp 242–243° C.

The starting material, 2-benzhydrilydene-amino-3-[6-(pyridin-3-yl)-pyridin-3-yl]-propionic acid ethyl ester is prepared from 2-benzhydrilydene-amino-3-(6-bromo-pyridin-3-yl)-propionic acid ethyl ester and pyridine-3-boronic acid; $^1$H NMR (250 MHz, CDCl$_3$) δ9.11 (d, 1H), 8.60 (dd, 1H), 8.41 (d, 1H), 8.25 (dt, 1H), 7.57 (dd, 2H), 7.48 (dd, 1H), 7.24–7.40 (m, 8H), 6.72 (d, 2H), 4.27 (dd, 1H), 4.18 (dq, 2H), 3.17–3.33 (ABX m, 2H), 1.25 (t, 3H).

(o)

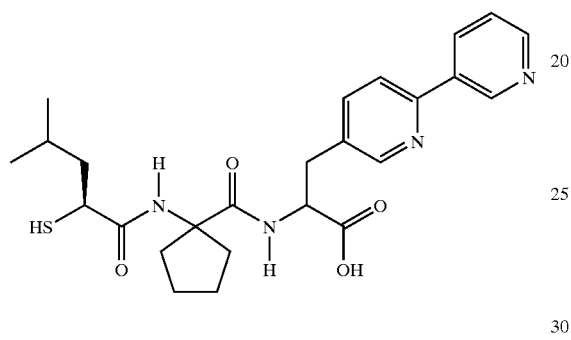

2-{[1-(2-Mercapto-4-methyl-pentanoylamino)-cyclopentanecarbonyl]-amino}-3-[6-(pyridin-3-yl)-pyridin-3-yl]-propanoic acid; mp 165–168° C.

(p)

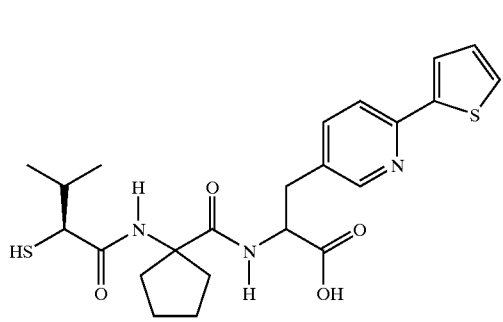

2-{[1-(2-Mercapto-3-methyl-butanoylamino)-cyclopentanecarbonyl]-amino}-3-[6-(thien-2-yl)-pyridin-3-yl]-propionic acid; mp 229–231° C.

The intermediate, 2-benzhydrilydene-amino-3-[6-(thien-2-yl)-pyridin-3-yl]-propionic acid ethyl ester is prepared from 2-benzhydrilydene-amino-3-(6-bromo-pyridin-3-yl)-propionic acid ethyl ester and thiophene-2-boronic acid; $^1$H NMR (250 MHz, CDCl$_3$) δ8.26 (d, 1H), 7.61 (d, 1H), 7.90 (dd, 1H), 7.47–7.52 (m, 2H), 7.26–7.41 (m, 8H), 7.08 (dd, 1H), 6.74 (d, 2H), 4.13–4.29 (dd and dq, 3H), 3.13–3.31 (ABX m, 2H), 1.26 (t, 3H).

(q)

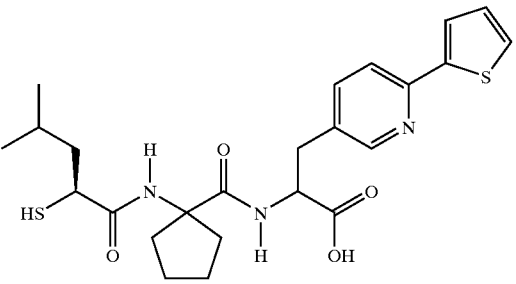

2-{[1-(2-Mercapto-4-methyl-pentanoylamino)-cyclopentanecarbonyl]-amino}-3-[6-(thien-2-yl)-pyridin-3-yl]-propionic acid; mp 190–200° C.

(r)

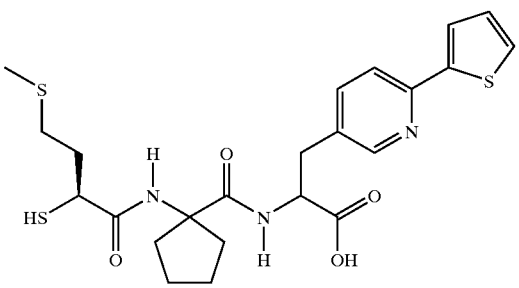

2-{[1-(2-Mercapto-4-methylthio-butanoylamino)-cyclopentanecarbonyl]-amino}-3-[6-(thien-2-yl)-pyridin-3-yl]-propionic acid; mp 175–177° C.

(s)

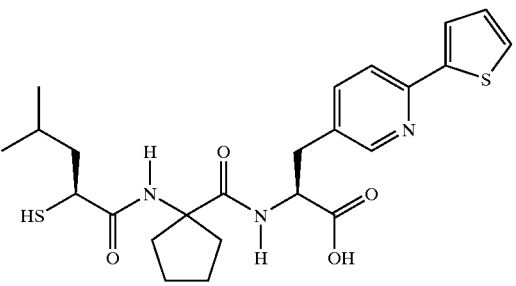

2-{[1-(2-Mercapto-4-methyl-pentanoylamino)-cyclopentanecarbonyl]-amino}-3-[6-(thien-2-yl)-pyridin-3-yl]-propionic acid; mp 221–222° C.

(t)

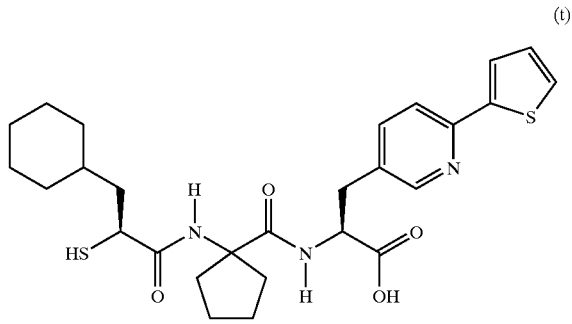

2-{[1-(3-Cyclohexyl-2-mercapto-butanoylamino)-cyclopentanecarbonyl]-amino}-3-[6-(thien-2-yl)-pyridin-3-yl]-propionic acid; mp 209–210° C.

(u)

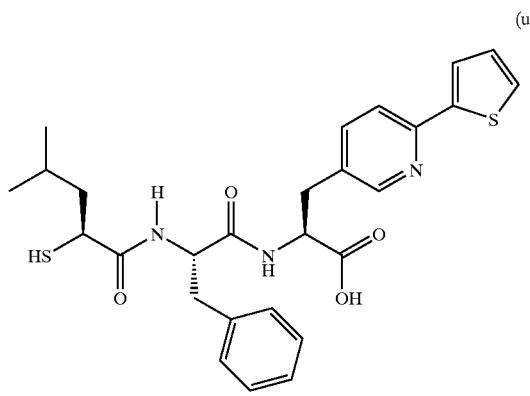

2-[1-(2-Mercapto-4-methyl-pentanoylamino)-3-phenyl-propionylamino]-3-[6-(thien-2-yl)-pyridin-3-yl]-propionic acid; mp 209–210° C.

(v)

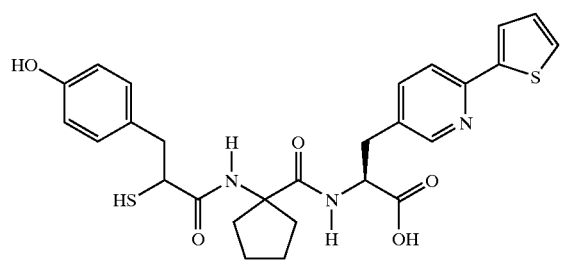

2-({1-[3-(4-Hydroxy-phenyl)-2-mercapto-propanoylamino]-cyclopentanecarbonyl}-amino)-3-[6-(thien-2-yl)-pyridin-3-yl]-propionic acid; mp 219–220° C.

(w)

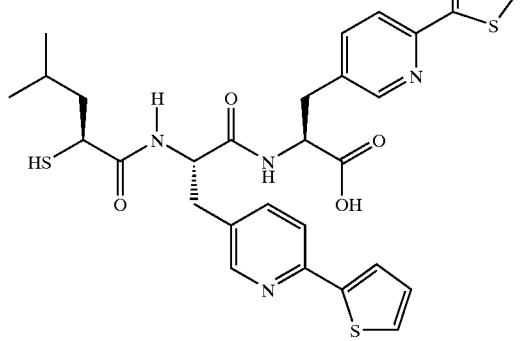

2-{2-(2-Mercapto-4-methyl-pentanoylamino)-3-[6-(thiophen-2-yl)-pyridin-3-yl]-propanoylamino}-3-[6-(thien-2-yl)-pyridin-3-yl]-propionic acid; starting from N-Boc-2-amino-3-[6-(thien-2-yl-pyridin-3-yl] propanoic acid instead of N-Boc-cycloleucine; mp 210–212° C.

(x)

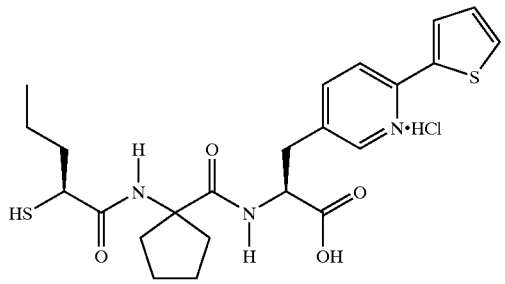

2-{[1-(2-Mercapto-pentanoylamino)-cyclopentanecarbonyl]-amino}-3-[6-(thien-2-yl)-pyridin-3-yl]-propionic acid hydrochloride; mp 165–167° C.

(y)

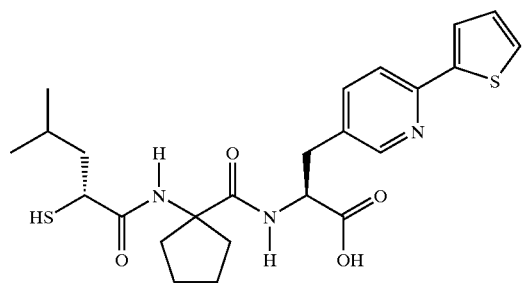

2-{[1-(2-Mercapto-4-methyl-pentanoylamino)-cyclopentanecarbonyl]-amino}-3-[6-(thien-2-yl)-pyridin-3-yl]-propionic acid; mp 190–192° C.

(z)

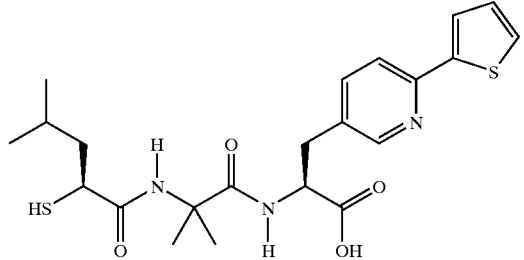

2-[2-(2-Mercapto-4-methyl-pentanoylamino)-2-methyl-propionylamino]-3-[6-(thien-2-yl)-pyridin-3-yl]-propionic acid; mp 194–196° C.; starting from N-Boc-2-amino-2-methyl-propionic acid instead of N-Boc-cycloleucine.

(aa)

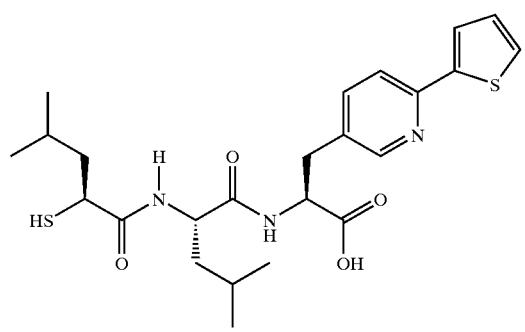

2-[2-(2-Mercapto-4-methyl-pentanoylamino)-4-methyl-pentanoylamino]-3-[6-(thien-2-yl)-pyridin-3-yl]-propionic acid; starting from N-Boc-2-amino-4-methyl-pentanoic acid instead of N-Boc-cycloleucine; mp 156–158° C.

(bb)

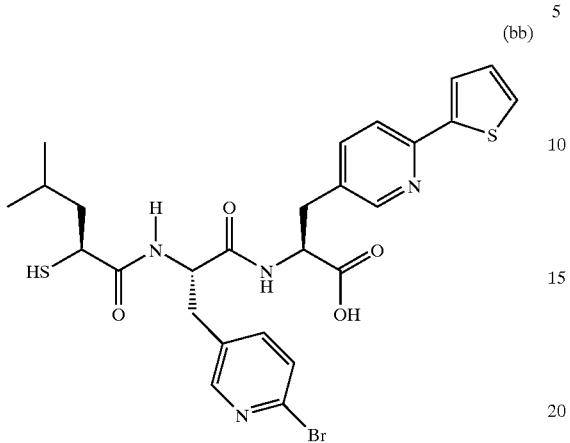

2-[3-(6-Bromo-pyridin-3-yl)-2-(2-mercapto-4-methyl-pentanoylamino)-propionylamino]-3-[6-(thien-2-yl)-pyridin-3-yl]-propionic acid; starting from N-Boc-2-amino-3-(6-bromo-pyridin-3-yl)-propionic acid instead of N-Boc-cycloleucine; mp 194–195° C.

(cc)

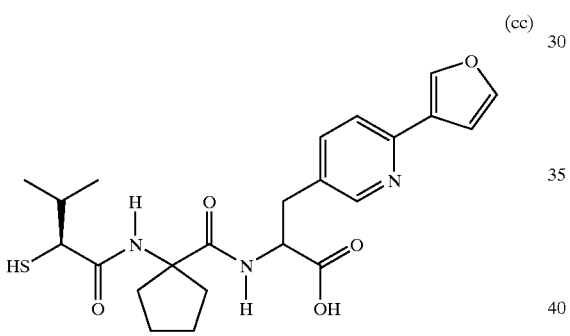

3-[6-(Furan-3-yl)-pyridin-3-yl]-2-{[1-(2-mercapto-3-methyl-butanoylamino)-cyclopentanecarbonyl]-amino}-propionic acid; mp 191–193° C.

The intermediate, 2-benzhydrylidene-amino-3-[6-(furan-3-yl)-pyridin-3-yl]-propionic acid ethyl ester is prepared from 2-benzhydrylidene-amino-3-(6-bromo-pyridin-3-yl)-propionic acid ethyl ester and 3-(4,4,5,5,-tetramethyl-[1,3,2]-dioxaborolan-2-yl)-furan; $^1$H NMR (250 MHz, CDCl$_3$) δ8.27 (d, 1H), 7.95 (d, 1H), 7.59 (s, 1H), 7.56 (d, 1H), 7.46 (dd, 1H), 7.24–7.39 (m, 8H), 6.83 (d, 1H), 6.26 (dd, 2H), 4.06–4.26 (m, 3H), 3.12–3.28 (m, 2H), 1.24 (t, 3H).

3-(4,4,5,5-Tetramethyl-[1,3,2]-dioxaborolan-2-yl)-furan is prepared as follows:

t-BuLi (40 mL of 1.7 M solution, 68 mmol) is added dropwise to a solution of 3-bromofuran (5.0 g, 34 mmol) in 100 mL of THF at −78° C., and the reaction mixture is stirred at −78° C. for 5 min. B(O-i-Pr)3 (23 mL, 100 mmol) is added, the cooling bath is removed, and the reaction mixture is stirred at room temperature for 18 h, and then cooled to 0° C. The reaction mixture is then quenched with 50 mL of 2N HCl, and extracted three times with EtOAc. The organic phases are combined, and washed with brine, dried over MgSO$_4$, filtered, and concentrated. The residue is dissolved in 200 mL of CH$_2$Cl$_2$. Pinnacol (20 g), and Na$_2$SO$_4$ (100 g) are added, and the mixture is stirred at room temperature overnight, and then filtered. The solution is concentrated and purified by chromatography on silica gel (gradient elution with 10–40% EtOAc/hexane) to provide the desired product as a yellow solid; mp 52–55° C.; $^1$H NMR (250 MHz, CDCl$_3$) δ7.78 (s, 1H), 7.46 (dd, 1H), 6.59 (d, 1H), 1.32 (s, 12H); IR (CH$_2$Cl$_2$, cm$^{-1}$) 1300, 1269, 1138.

(dd)

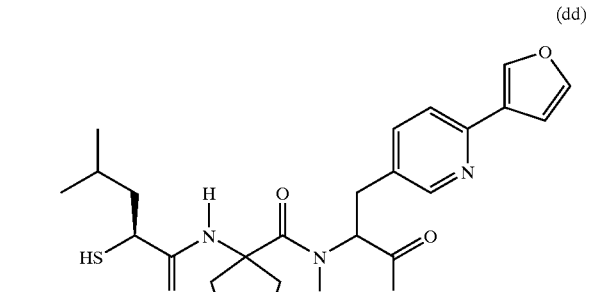

3-[6-(Furan-3-yl)-pyridin-3-yl]-2-{[1-(2-mercapto-4-methyl-pentanoylamino)-cyclopentanecarbonyl]-amino}-propanoic acid; mp 190–193° C.

(ee)

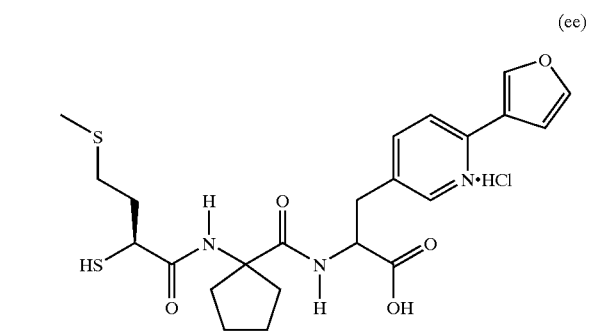

3-[6-(Furan-3-yl)-pyridin-3-yl]-2-{[1-(2-mercapto-4-methylthio-butanoylamino)-cyclopentanecarbonyl]-amino}-propanoic acid hydrochloride; mp 150–153° C.

(ff)

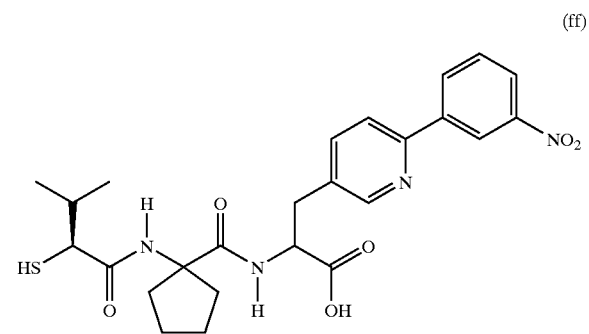

2-{[1-(2-Mercapto-3-methyl-butanoylamino)-cyclopentanecarbonyl]-amino}-3-[6-(3-nitro-phenyl)-pyridin-3-yl]-propionic acid; mp 210–213° C.

The intermediate, 2-(benzhydrylidene-amino)-3-[6-(3-nitro-phenyl)-pyridin-3-yl]-propionic acid ethyl ester is prepared from 2-benzhydrylidene-amino-3-(6-bromo-pyridin-3-yl)-propionic acid ethyl ester and 3-nitro-phenylboronic acid; $^1$H NMR (250 MHz, CDCl$_3$) δ8.82 (t, 1H), 8.45 (d, 1H), 8.33 (dd, 1H), 8.25 (dd, 1H), 7.50–7.70 (m, 5H), 7.30–7.46 (m, 6H), 6.75 (d, 2H), 4.16–4.38 (m, 3H), 3.24–3.40 (m, 2H), 1.25 (t, 3H).

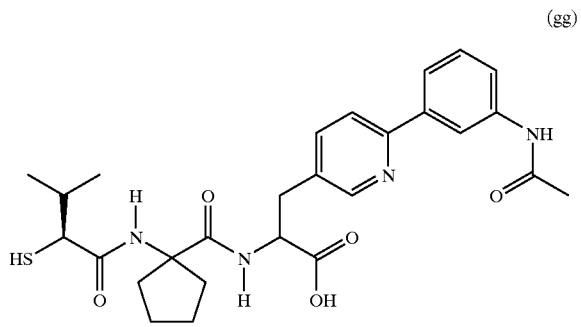
(gg)

3-[6-(3-Acetylamino-phenyl)-pyridin-3-yl]-2-{[1-(2-mercapto-3-methyl-butanoylamino)-cyclopentanecarbonyl]-amino}-propanoic acid; mp 148–149° C.

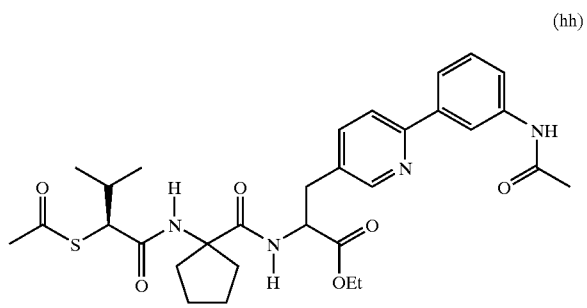
(hh)

3-[6-(3-Acetylamino-phenyl)-pyridin-3-yl]-2-{[1-(2-acetylthio-3-methyl-butanoylamino)-cyclopentanecarbonyl]-amino}-propanoic acid ethyl ester.

Acetyl chloride (11.5 mL) is added to a solution of 2-{[1-(2-acetylthio-3-methyl-butanoylamino)-cyclopentanecarbonayl]-amino}-3-[6-(3-amino-phenyl)-pyridin-3-yl]-propanoic acid ethyl ester (78 mg) in 4 mL of THF at 0° C. The cooling bath is removed, and the reaction mixture is stirred for 2 days, and then concentrated in vacuo. The residue is purified by chromatography on silica gel (0.5% MeOH/EtOAc) to yield the product; $^1$H NMR (250 MHz, CDCl$_3$) δ8.45 (d, 1H), 8.00 (s,1H), 7.65–7.95 (m, 3H), 7.62 (d, 1H), 7.28–7.40 (m, 1H), 7.12 (d, 1H), 6.85, 6.48 (s each, total 1H), 4.68–4.82 (m, 1H), 4.50 (br s, 1H), 4.06–4.25 (m, 2H), 3.60–3.90 (m, 1H), 3.10–3.35 (m, 2H), 2.35 (s, 3H), 2.20 (s, 3H), 1.50–2.40 (m, 9H), 1.19 (t, 3H), 0.88–1.00 (m, 6H).

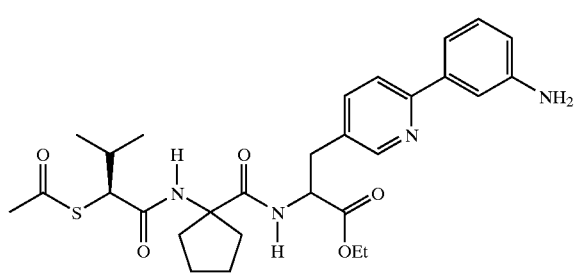
(ii)

2-{[1-(2-Acetylthio-3-methyl-butanoylamino)-cyclopentanecarbonyl]-amino}-3-[6-(3-amino-phenyl)-pyridin-3-yl]-propionic acid ethyl ester.

A suspension of 2-{[1-(2-acetylthio-3-methyl-butanoylamino)-cyclopentanecarbonyl]-amino}-3-[6-(3-nitro-phenyl)-pyridin-3-yl]-propanoic acid ethyl ester (110 mg) and 25 mg of 10% Pd/C in 10 mL of EtOH is stirred under a H$_2$ atmosphere for 18 h. The catalyst is filtered off, and the reaction mixture is concentrated in vacuo. The residue is purified by chromatography on silica gel (50% EtOAc/hexane) to produce yellow product; $^1$H NMR (250 MHz, CDCl$_3$) δ8.39 (d, 1H), 7.60 (s, 2H), 7.10–7.36 (m, 3H), 6.71 (d, 1H), 6.34 (d, 1H), 4.76 (app q, 1H), 4.15 (q, 2H), 3.62 (dd, 1H), 3.05–3.25 (m, 2H), 2.35, 2.32 (two s, 3H), 1.55–2.40 (m, 9H), 1.19 (t, 3H), 0.92–1.06 (m, 6H).

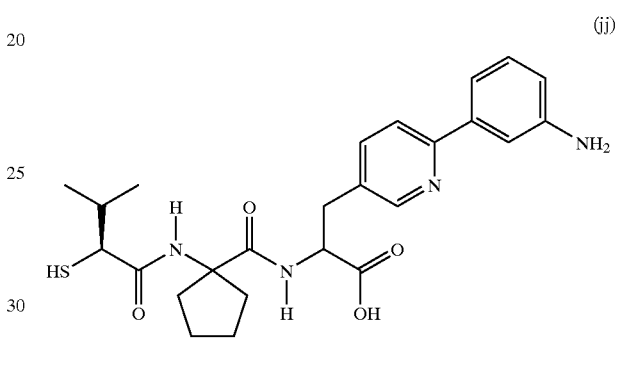
(jj)

3-[6-(3-Aminophenyl)-pyridin-3-yl]-2-{[1-(2-mercapto-3-methyl-butanoylamino)-cyclopentanecarbonyl]-amino}-propionic acid; mp 172–176° C.

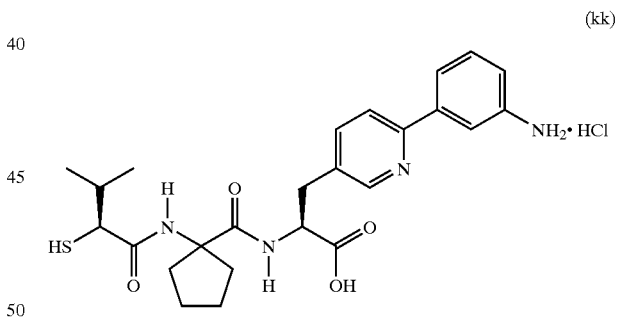
(kk)

3-[6-(3-Amino-phenyl)-pyridin-3-yl]-2-{[1-(2-mercapto-3-methyl-butanoylamino)-cyclopentanecarbonyl]-amino}-propionic acid hydrochloride; mp 162–164° C.

The starting material is prepared as follows:

(S)-2-Amino-5-[6-(3-nitrophenyl)-pyridin-3-yl]-propionic acid methyl ester dihydrochloride is prepared from 5-[6-(3-nitrophenyl)-pyridin-3-ylmethyl]-2-tert-butyl-3-methyl-4-oxo-imidazolidine-1-carboxylic acid tert-butyl ester according to the procedure reported by Seebach and Fitzi (*Tetrahedron* 1988, 44, 5277), followed by standard esterification with MeOH and HCl; mp 123–126° C.

The intermediate of the formula

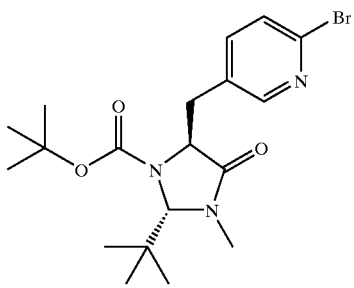

namely 5-(6-bromo-pyridin-3-ylmethyl)-2-tert-butyl-3-methyl-4-oxo-imidazolidine-1-carboxylic acid tert-butyl ester, is prepared from 2-bromo-5-bromomethyl-pyridine according to the procedure reported by Seebach and Fitzi (*Tetrahedron* 1988, 44, 5277); mp 164–165° C.

The above intermediate is converted to the compound of the formula

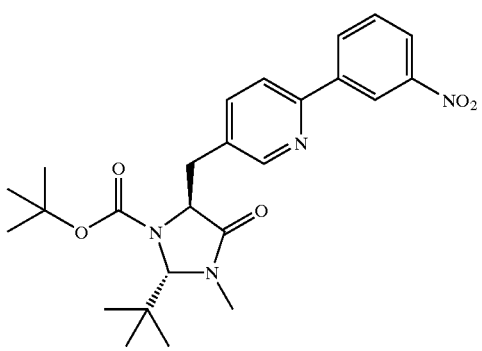

namely 5-[6-(3-nitro-phenyl)-pyridin-3-ylmethyl]-2-tert-butyl-3-methyl-4-oxo-imidazolidine-1-carboxylic acid tert-butyl ester according to the Suzuki coupling procedure; oil; $^1$H NMR (300 MHz, CDCl$_3$) δ8.83 (d, 1H), 8.52 (s, 1H), 8.35 (d, 1H), 8.24 (dd, 1H), 7.61–7.66 (m, 3H), 4.66 (br s, 1H), 4.40 (br d, 1H), 3.80–4.00 (br m, 1H), 3.30 (dd, 1H), 2.87 (s, 3H), 1.51 (s, 9H), 0.95 (s, 9H).

(II)

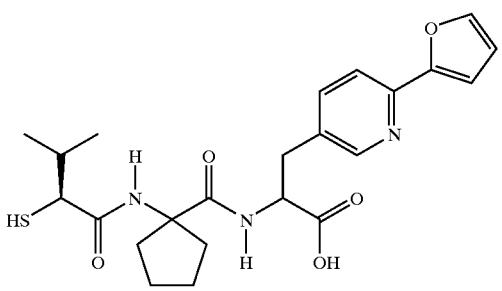

3-[6-(Furan-2-yl)-pyridin-3-yl]-2-{[1-(2-mercapto-3-methyl-butanoylamino)-cyclopentanecarbonyl]-amino}-propionic acid; mp 215–220° C.

The starting material

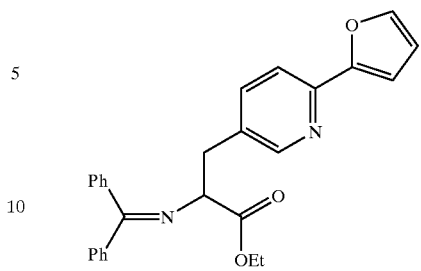

namely 2-benzhydrilydene-amino-3-[6-(furan-2-yl)-pyridin-3-yl]-propionic acid ethyl ester, is prepared as follows:

A solution of Pd$_2$(dba)$_3$ (0.54 g) and PPh$_3$ (1.28 g) in 50 mL of dioxane is stirred for 15 min, and then added to a solution of 2-benzhydrylidene-amino-3-(6-bromo-pyridin-3-yl)-propionic acid ethyl ester (3.0 g, 6.86 mmol), 2-tri-n-butylstannyl-furan (4.80 g, 13.72 mmol), LiCl (0.13 g), and ammonium formate (0.60 g) in 25 mL of dioxane, and the reaction mixture is heated at 80° C. for 18 h, cooled to room temperature, and concentrated. The residue is dissolved in EtOAc, filtered, and concentrated. The crude product is purified by chromatography on silica gel (33% EtOAc/hexane) to furnish the desired product; $^1$H NMR (250 MHz, CDCl$_3$) δ8.29 (d, 1H), 7.58 (dd, 2H), 7.49 (q, 1H), 7.20–7.40 (m, 8H), 6.96 (t, 1H), 6.73 (br d, 2H), 6.49 (app q, 1H), 4.11–4.31 (m, 3H), 3.10–3.28 (m, 2H), 1.20 (t, 3H).

(mm)

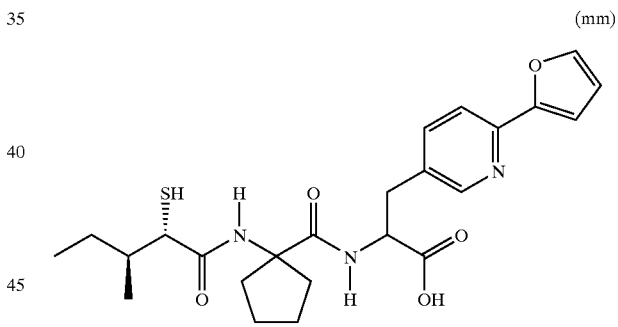

3-[6-(Furan-2-yl)-pyridin-3-yl]-2-{[1-(2-mercapto-3-methyl-pentanoylamino)-cyclopentanecarbonyl]-amino}-propionic acid; mp 202–204° C.

(nn)

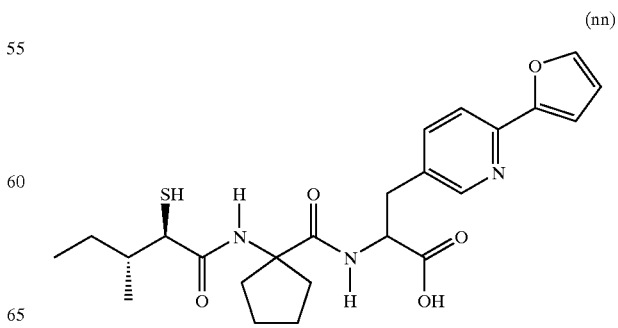

3-[6-(Furan-2-yl)-pyridin-3-yl]-2-{[1-(2-mercapto-3-methyl-pentanoylamino)-cyclopentanecarbonyl]-amino}-propionic acid; mp 175–180° C.

3-[6-(Furan-2-yl)-pyridin-3-yl]-2-{[1-(2-mercapto-4-methyl-pentanoylamino)-cyclopentanecarbonyl]-amino}-propionic acid; mp 200–202° C.

(oo)

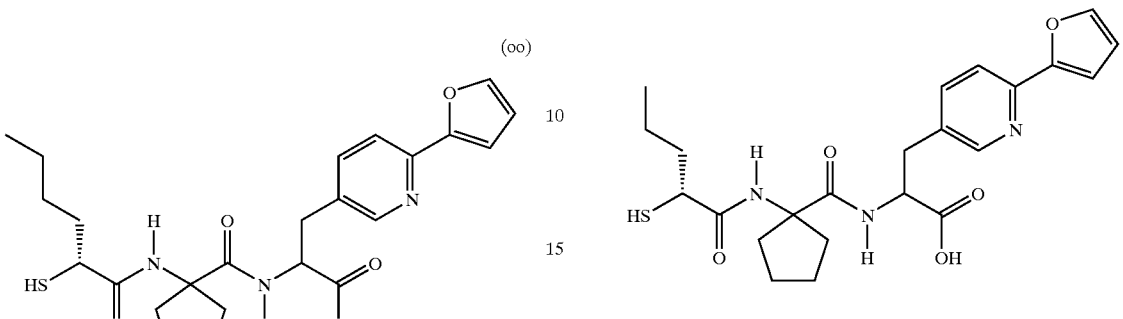

(rr)

3-[6-(Furan-2-yl)-pyridin-3-yl]-2-{[1-(2-mercapto-pentanoylamino)-cyclopentanecarbonyl]-amino}-propionic acid; mp 200–202° C.

3-[6-(Furan-2-yl)-pyridin-3-yl]-2-{[1-(2-mercapto-hexanoylamino)-cyclopentanecarbonyl]-amino}-propionic acid; mp 185–189° C.

(pp)

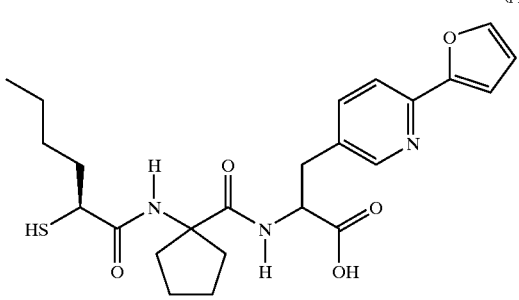

(ss)

3-[6-(Furan-2-yl)-pyridin-3-yl]-2-{[1-(2-mercapto-pentanoylamino)-cyclopentanecarbonyl]-amino}-propionic acid; mp 205–207° C.

3-[6-(Furan-2-yl)-pyridin-3-yl]-2-{[1-(2-mercapto-hexanoylamino)-cyclopentanecarbonyl]-amino}-propionic acid; mp 187–191° C.

(tt)

3-[6-(Furan-2-yl)-pyridin-3-yl]-2-{[1-(2-mercapto-4-methylthiobutanoylamino)-cyclopentanecarbonyl]-amino}-propionic acid; mp 195–197° C.

(qq)

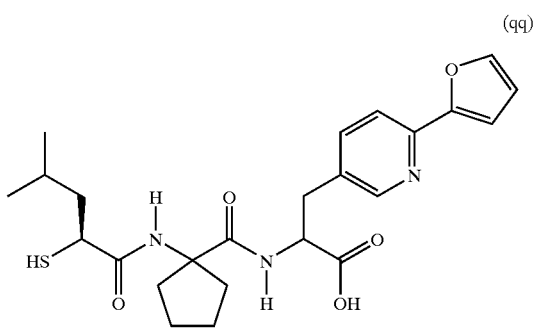

(uu)

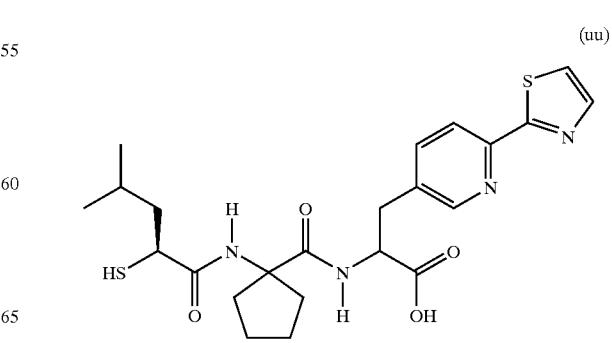

2-{[1-(2-Mercapto-4-methyl-pentanoylamino)-cyclopentanecarbonyl]-amino}-3-[6-(thiazol-2-yl)-pyridin-3-yl]-propionic acid; mp 185–187° C.

The starting material, 2-benzhydrilydene-amino-3-[6-(thiazol-2-yl)-pyridin-3-yl]-propionic acid ethyl ester is prepared from 2-benzhydrilydene-amino-3-(6-bromo-pyridin-3-yl)-propionic acid ethyl ester and 2-tri-n-butylstannyl-thiazole similarly to the procedure described above for the coupling of 2-tri-n-butylstannyl-furan. $^1$H NMR (250 MHz, CDCl$_3$) δ8.26 (d, 1H), 7.95 (d, 1H), 7.82 (d, 1H), 7.51 (dt, 2H), 7.43 (dd, 1H), 7.19–7.38 (m, 7H), 6.68 (br d, 2H), 4.00–4.24 (m, 3H), 3.08–3.28 (m, 2H), 1.19 (t, 3H).

Example 3

(a)

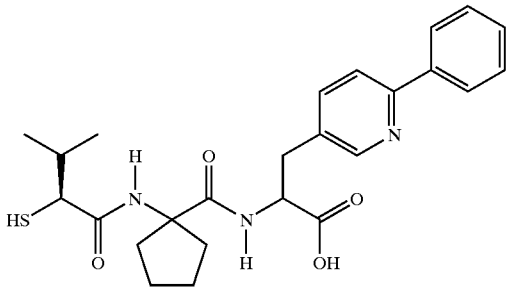

2-{[1-(2-Mercapto-3-methyl-butanoylamino)-cyclopentanecarbonyl]-amino}-3-(6-phenyl-pyridin-3-yl)-propionic acid is prepared using 3-(6-bromo-pyridin-3-yl)-2-[(1-tert-butoxycarbonylamino-cyclopentanecarbonyl)-amino]-propionic acid ethyl ester for the Suzuki coupling reaction; mp 208–211° C.

The starting material, 3-(6-bromo-pyridin-3-yl)-2-[(1-tert-butoxycarbonylamino-cyclopentanecarbonyl)-amino]-propionic acid ethyl ester is prepared from 2-benzhydrilydene-amino-3-(6-bromo-pyridin-3-yl)-propionic acid ethyl ester according to previously described procedures; white solid; $^1$H NMR (300 MHz, CDCl$_3$) δ8.08 (s, 1H), 7.36 (dd, 2H), 4.75 (app q, 1H), 4.14 (q, 2H), 3.15 (dd, 1H), 3.05 (dd, 1H), 2.05–2.40 (m, 2H), 1.60–2.40 (m, 8H), 1.41 (s, 9H), 1.25 (t, 3H).

The intermediate

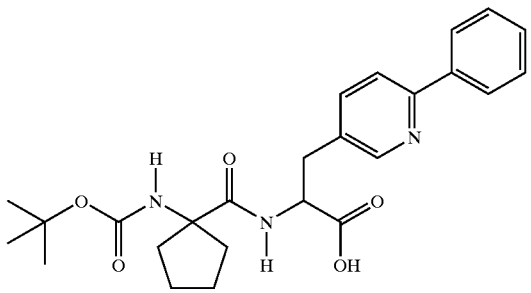

namely 2-[(1-tert-butoxycarbonylamino-cyclopentanecarbonyl)-amino]-3-[6-(2-methoxy-phenyl)-pyridin-3-yl]-propionic acid ethyl ester, is prepared by a Suzuki coupling reaction as follows:

A suspension of PhB(OH)$_2$ (50 mg, 0.413 mmol), 3-(6-bromo-pyridin-3-yl)-2-[(1-tert-butoxycarbonylamino-cyclopentanecarbonyl)-amino]-propionic acid ethyl ester (100 mg, 0.206 mmol), PdCl$_2$(dppf) (25 mg, 0.031 mmol), and K$_3$PO$_4$ in 10 mL of DME is heated at 85° C. for 18 h, and then cooled to room temperature. The reaction mixture is then partitioned between water and EtOAc. The organic phase is separated, and washed with brine, dried over Na2SO$_4$, filtered, and concentrated. The residue is purified by chromatography on silica gel (33% EtOAc/hexane) to provide the product as a white solid; $^1$H NMR (300 MHz, CDCl$_3$) δ8.40 (br s,1H), 7.93 (dd, 2H), 7.56–7.70 (m, 2H), 7.30–7.50 (m, 3H), 4.87 (app q, 1H), 4.78 (br s, 1H), 4.06–4.24 (m, 2H), 3.08–3.24 (m, 2H), 2.05–2.40 (m, 2H), 1.65–1.88 (m, 6H), 1.41 (s, 9H), 1.20 (t, 3H).

Similarly prepared is:

(b)

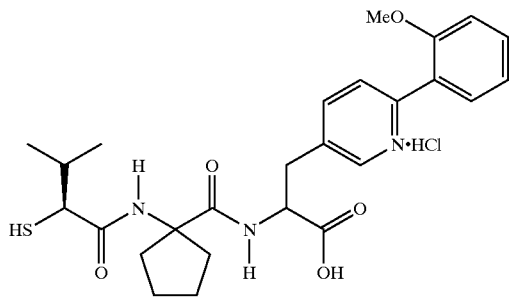

2-{[1-(2-Mercapto-3-methyl-butanoylamino)-cyclopentanecarbonyl]-amino}-3-[6-(2-methoxy-phenyl)-pyridin-3-yl]-propanoic acid hydrochloride; mp 133–134° C.

The starting material, 2-[(1-tert-butoxycarbonylamino-cyclopentanecarbonyl)-amino]-3-[6-(2-methoxy-phenyl)-pyridin-3-yl]-propionic acid ethyl ester is prepared from 2-methoxy-phenylboronic acid; $^1$H NMR (300 MHz, CDCl$_3$) δ8.44 (br s, 1H), 7.70–7.80 (m, 2H), 7.55 (br d, 1H), 7.37 (dt, 1H), 7.07 (t, 1H), 6.99 (d, 1H), 4.90 (app q, 1H), 4.80 (br s, 1H), 4.17 (q, 2H), 3.85 (s, 3H), 3.08–3.22 (m, 2H), 2.05–2.40 (m, 2H), 1.65–1.85 (m, 6H), 1.41 (s, 9H), 1.23 (t, 3H).

What is claimed is:

1. A compound of the formula

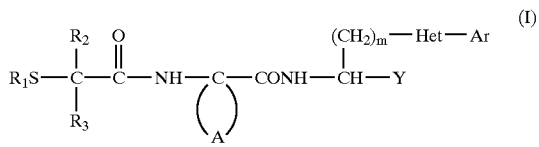

or of the formula Ia

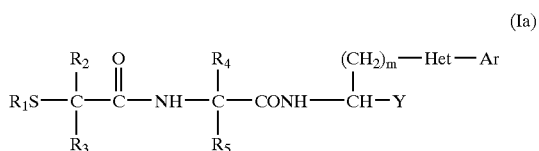

wherein

Het represents monocyclic heterocyclic aryl;

Ar represents carbocyclic or heterocyclic aryl;

R$_1$ represents hydrogen or acyl;

R$_2$ represents hydrogen, lower alkyl, carbocyclic or heterocyclic aryl, carbocyclic or heterocyclic aryl-lower alkyl, cycloalkyl, cycloalkyl-lower alkyl, biaryl, biaryl-lower alkyl, (hydroxy, lower alkoxy or acyloxy)-lower alkyl, or lower alkyl-(thio, sulfinyl or sulfonyl)-lower alkyl;

R$_3$ represents hydrogen or lower alkyl; or R$_2$ and R$_3$ together with the carbon atom to which they are attached represent cycloalkylidene or benzo-fused cycloalkylidene;

$R_4$ represents hydrogen, lower alkyl, substituted alkyl, aryl-lower alkyl or biaryl-lower alkyl;

$R_5$ represents lower alkyl, substituted alkyl, aryl-lower alkyl or biaryl-lower alkyl;

A together with the carbon atom to which it is attached forms a ring and represents 5- to 10-membered cycloalkenylidene radical which may be substituted by lower alkyl or aryl-lower alkyl or may be fused to a saturated or unsaturated carbocyclic 5- to 7-membered ring; or A together with the carbon to which it is attached represents 5- to 6-membered oxacycloalkylidene, thiacycloalkylidene or azacycloalkylidene optionally substituted by lower alkyl or aryl-lower alkyl; or A together with the carbon atom to which it is attached represents 2,2-norbonylidene;

m is zero or 1–3;

Y represents 5-tetrazolyl, carboxyl or carboxyl derivatized in form of a pharmaceutically acceptable ester;

a disulfide derivative derived from a said compound wherein $R_1$ is hydrogen; or a pharmaceutically acceptable salt thereof.

2. A compound according to claim 1 wherein the asymmetric carbon with substituent Y has the S-configuration.

3. A compound according to claim 1 wherein Het represents thienyl, furanyl, oxazolyl, pyridyl, thiazolyl or oxadiazolyl, each optionally substituted by lower alkyl.

4. A compound according to claim 1 wherein Ar represents monocyclic carbocyclic aryl or monocyclic heterocyclic aryl.

5. A compound according to claim 2 of the formula

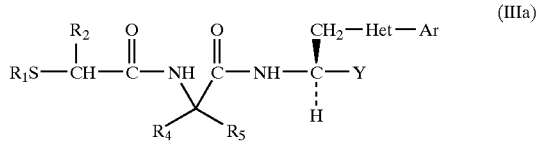

(IIIa)

wherein Het represents pyridyl, pyrimidinyl, thienyl, furanyl, oxazolyl, isoxazolyl, oxadiazolyl or thiazolyl, each optionally substituted by lower alkyl;

Ar represents monocyclic carbocyclic aryl or monocyclic heterocyclic aryl;

$R_1$ represents hydrogen, lower alkanoyl, methoxy-lower alkanoyl, benzoyl or pyridylcarbonyl;

$R_2$ represents $C_2$–$C_5$-alkyl, cyclohexylmethyl or $C_2$–$C_4$-alkyl interrupted by O or S;

$R_4$ and $R_5$ represent lower alkyl or lower alkyl substitued by lower alkoxycarbonyl, lower alkanoyloxy, lower alkanoylthio, lower alkoxy, lower alkylthio, hydroxy, di-lower alkylamino, lower alkanoylamino, morpholino, piperidino, pyrrolidino or 1-lower alkylpiperazino;

Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

6. A compound according to claim 2

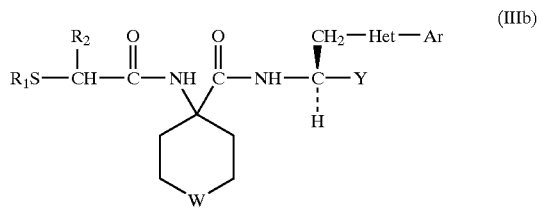

(IIIb)

wherein

Het represents pyridyl, pyrimidinyl, thienyl, furanyl, oxazolyl, isoxazolyl, oxadiazolyl or thiazolyl, each optionally substituted by lower alkyl;

Ar represents monocyclic carbocyclic aryl or monocyclic heterocyclic aryl;

W represents O, S or $NR_6$ in which $R_6$ is hydrogen, acyl, lower alkyl or aryl-lower alkyl;

$R_1$ represents hydrogen, lower alkanoyl, methoxy-lower alkanoyl, benzoyl or pyridylcarbonyl;

$R_2$ represents $C_2$–$C_5$-alkyl, cyclohexylmethyl or C2–C4-alkyl interrupted by O or S;

Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

7. A compound according to claim 5 wherein Het represents 3-pyridyl, 2-, 4- or 5-pyrimidinyl, 2- or 3-thienyl, 2- or 3-furanyl, 4- or 5-oxazolyl, 3-, 4- or 5-isoxazolyl, or 4- or 5-thiazolyl, each optionally substituted by lower alkyl; Ar represents monocyclic carbocyclic or heterocyclic aryl; R1 represents hydrogen or lower alkanoyl; $R_2$ represents $C_3$–$C_5$-alkyl; Y represents 5-tetrazolyl, carboxyl, lower alkoxycarbonyl, benzyloxycarbonyl, pyridylmethoxycarbonyl, a-(lower alkanoyloxy-, lower alkoxycarbonyl- or di-lower alkylaminocarbonyl-) lower alkoxycarbonyl; or a pharmaceutically acceptable salt thereof.

8. A compound according to claim 2 of the formula

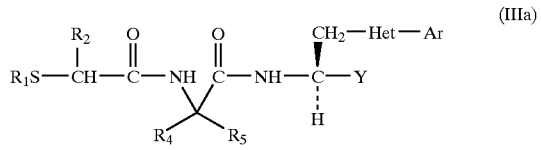

(IIIa)

wherein

Het represents pyridyl, thienyl, oxazolyl, oxadiazolyl or thiazolyl each optionally substituted by lower alkyl;

Ar represents phenyl or phenyl substituted by one or more substituents selected from the group consisting of halogen, lower alkoxy, nitro, amino and lower alkanoyl-amino;

$R_1$ represents hydrogen or lower alkanoyl;

$R_2$ represents lower alkyl or lower alkyl substituted by lower alkylthio, phenyl, phenyl substituted by hydroxy, or cyclohexyl;

$R_4$ is hydrogen or lower alkyl;

$R_5$ is lower alkyl, phenyl-lower alkyl or pyridyl-lower alkyl in which the pyridyl moiety is substituted by halogen or thienyl; and Y represents carboxyl or lower alkoxycarbonyl; or a pharmaceutically acceptable salt thereof.

9. A compound according to claim 5 wherein Ar-Het in combination represents 5-Ar-(2- or 3-thienyl), 2-Ar-(4- or 5-oxazolyl), 2-Ar-(4- or 5-thiazolyl), 5-Ar-(3-[1,2,4]oxadiazolyl), 6-Ar-3-pyridyl or 5-Ar-(2- or 3-furanyl); and Ar represents monocyclic carbocyclic aryl, thienyl, furanyl, pyridyl, thiazolyl, isoxazolyl, oxazolyl or pyrimidinyl.

10. A compound according to claim 8 wherein Ar-Het combined represents 5-phenyl-2-thienyl, 4-phenyl-2-thienyl, 4-methyl-2-phenyl-5-oxazolyl, 2-(3-chloro-4-fluorophenyl)-5-thiazolyl, 5-(3,5-dimethyl-4-isoxazolyl)-3-[1,2,4]oxadiazolyl, 6-(3-thienyl)-3-pyridinyl, 6-(3-pyridinyl)-3-pyridinyl, 6-(2-thienyl)-3-pyridinyl, 6-(3-furanyl)-3-pyridinyl, 6-(3-nitrophenyl)-3pyridinyl, 6-(3-acetylaminophenyl)-3-pyridinyl, 6-(3-aminophenyl)-3-pyridinyl, 6-(2-furanyl)-3-pyridinyl, 6-(2-thiazolyl)-3-pyridinyl, 6-(2-methoxyphenyl)-3-pyridinyl or 6-phenyl-3-pyridinyl.

11. A compound according to claim 1 wherein Het represents 3-pyridyl, 2-, 4- or 5-pyrimidinyl, 2- or 3-thienyl, 2- or 3-furanyl, 4- or 5-oxazolyl, 3-, 4- or 5-isoxazolyl or 4- or 5-thiazolyl, each optionally substituted by lower alkyl; Ar represents monocyclic carbocyclic or heterocyclic aryl; $R_1$ represents hydrogen or lower alkanoyl; $R_2$ represents $C_3$–$C_5$-alkyl; Y represents 5-tetrazolyl, carboxyl, lower alkoxycarbonyl, benzyloxycarbonyl, pyridylmethoxycarbonyl, a-(lower alkanoyloxy-, lower alkoxycarbonyl- or di-lower alkylaminocarbonyl-) lower alkoxycarbonyl; or a pharmaceutically acceptable salt thereof.

12. A compound according to claim 5 wherein Het represents 3-pyridyl; Ar represents monocyclic carbocyclic or monocyclic heterocyclic aryl; $R_1$ represents hydrogen; $R_2$ represents $C_3$–$C_5$-alkyl, cyclohexylmethyl or $C_2$–$C_4$-alkyl interrupted by O or S; $R_4$ and $R_5$ represent lower alkyl; Y represents carboxyl; an ester and/or S-acyl prodrug derivative thereof; or a pharmaceutically acceptable salt thereof.

13. A compound according to claim 5 wherein Het represents 3-pyridyl; Ar represents phenyl or phenyl substituted by halogen, lower alkyl, lower alkoxy, nitro, amino or acylamino; or Ar represents 2- or 3-furanyl, 2- or 3-thienyl, 2-, 4- or 5-thiazolyl, 3-pyridyl, 2-, 4- or 5-oxazolyl, or 5-pyrimidinyl; $R_1$ represents hydrogen or lower alkanoyl; $R_2$ represents $C_3$–$C_5$-alkyl, cyclohexylmethyl, or $C_2$–$C_4$-alkyl interrupted by O or S; $R_4$ and $R_5$ represent $C_1$–$C_4$-straight chain alkyl; Y is 5-tetrazolyl, carboxyl or lower alkoxycarbonyl; or a pharmaceutically acceptable salt thereof.

14. A pharmaceutical composition comprising a compound according to claim 1 in combination with a pharmaceutically acceptable carrier.

15. A method of inhibiting endothelin coverting enzyme in a mammal which comprises administering enterally or parenterally to a mammal in need thereof an effective amount of a compound of claim 1.

16. A method of treating endothelin dependent hypertension in a mammal which comprises administering enterally or parenterally to a mammal in need thereof an effective endothelin converting enzyme inhibiting amount of a compound of claim 1.

* * * * *